(12) United States Patent
O'Malley et al.

(10) Patent No.: US 8,945,625 B2
(45) Date of Patent: Feb. 3, 2015

(54) REGULATED DELIVERY SYSTEMS FOR INNER EAR DRUG APPLICATION AND USES THEREOF

(71) Applicant: The Trustees of the University of Pennsylvania, Philadelphia, PA (US)

(72) Inventors: Bert W. O'Malley, Villanova, PA (US); Daqing Li, Wynnewood, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 91 days.

(21) Appl. No.: 13/723,950

(22) Filed: Dec. 21, 2012

(65) Prior Publication Data
US 2013/0189241 A1 Jul. 25, 2013

Related U.S. Application Data

(63) Continuation-in-part of application No. 12/747,452, filed as application No. PCT/US2008/086099 on Dec. 9, 2008.

(60) Provisional application No. 60/996,877, filed on Dec. 10, 2007.

(51) Int. Cl.
*A61K 9/00* (2006.01)
*A61K 9/06* (2006.01)
*A61K 47/36* (2006.01)
*A61K 47/42* (2006.01)

(52) U.S. Cl.
CPC .............. *A61K 9/0046* (2013.01); *A61K 9/0002* (2013.01); *A61K 9/06* (2013.01); *A61K 47/36* (2013.01); *A61K 47/42* (2013.01); *Y10S 514/956* (2013.01)
USPC ........ 424/488; 424/94.3; 424/94.61; 514/956

(58) Field of Classification Search
USPC ................................. 524/115; 424/94.61, 443
See application file for complete search history.

(56) References Cited

U.S. PATENT DOCUMENTS

2003/0158302 A1    8/2003   Chaput et al.

OTHER PUBLICATIONS

Ma et al., "Topical treatment with growth factors for tympanic membrane perforations: progress towards clinical application" Acta Otolaryngol 2002: 122; 586-599.
Buchwald et al. "Long-term, continuous intravenous heparin administration by an implantable infusion pump in ambulatory patients with recurrent venous thrombosis." Surgery 88:507 (1980).
Saudek et al."A preliminary trial of the programmable implantable medication system for insulin delivery." N. Engl. J. Med. 321:574 (1989).
Goodson, In Medical Applications of Controlled Release, supra, vol. 2, pp. 115-138 (1984).
Langer, "New methods of drug delivery", Science 249:1527-1533 (1990).
Katre et al. "Chemical modification of recombinant interleukin 2 by polyethylene glycol increases its potency in the murine Meth A sarcoma model" Proc Natl Acad Sci U S A. 84(6):1487-91. Mar. 1987.
Sefton, "Implantable pumps", CRC Crit. Ref. Biomed. Eng. 14:201 (1987).
Johnsen et al., << Isolation, characterization and heterologous expression of a novel chitosanase from *Janthinobacterium* sp. strain 4239 *Microbial Cell Factories* 2010, 9:5.

*Primary Examiner* — Walter Webb
(74) *Attorney, Agent, or Firm* — Mark S. Cohen; Pearl Cohen; Zedek Latzer Baratz LLP

(57) ABSTRACT

The invention relates to a controlled release delivery compositions and methods of using them for pathologies associated with Otorhinolaryngology and Head and Neck. Specifically, the invention relates to regulating drug delivery by the use of chitosan based matrices together with chitosanases.

29 Claims, 11 Drawing Sheets

REGULATED DELIVERY SYSTEMS FOR INNER EAR DRUG APPLICATION AND USES THEREOF

CROSS-REFERENCE TO RELATED APPLICATIONS

This application is a Continuation-in-Part of U.S. patent application Ser. No. 12/747,452, filed Jun. 10, 2010, which is a National Phase Application of PCT International Application, PCT/US2008/086099 filed Dec. 9, 2008, claiming priority to U.S. Provisional Patent Application 60/996,877, filed Dec. 10, 2007, each of which is incorporated by reference herein in its entirety.

FIELD OF THE INVENTION

The invention relates to controlled release delivery compositions and systems and methods of using them for pathologies associated with Otorhinolaryngology and Head and Neck, such as an inner ear disease.

BACKGROUND OF THE INVENTION

The effective medical treatment of inner ear disease depends upon achieving therapeutic concentrations of medications, such as dexamethasone or gentamicin, within the fluids and tissues of the inner ear. Drugs delivered to the inner ear are commonly administered systemically via the oral, intravenous, or intramuscular routes. However, systemic drug administration for focal disease of the inner ear is not ideal as this does not meet an important pharmacological principal in which local administration is preferred for local pathological processes.

Systemic drug administration increases the likelihood of systemic toxicities and side effects and creates an inequality in drug concentration with higher circulating levels in the serum but lower local levels at the inner ear where the drug is needed. Relatively large doses of a medication are therefore required to overcome the systemic volume of distribution in order to achieve a therapeutic drug concentration in the inner ear. In addition to the inherent risk of toxicities, responses to systemic administration vary considerably between patients. This is due, among other things, to inter-dose variability, differences in systemic volume of distribution, variability in the ability of a given drug to cross the blood-inner ear barrier, and factors affecting the half-life of the drug such as peripheral drug metabolism and drug clearance.

Intratympanic injection of streptomycin for the treatment of intractable vertigo in patients with Ménière's disease resulted in profound hearing loss in a significant proportion of patients. However, reported success in ameliorating Ménière's symptomology with intratympanic drug administration helped to popularize the concept of local drug administration to the inner ear. Indeed, it has become routine for otolaryngologists to perform intratympanic injections, and the efficacy of this approach versus systemic drug administration has been confirmed for various clinical indications.

However, there remains a considerable amount of variability in clinical outcomes among those patients treated with intratympanic injections. Several factors account for this variability. Drugs enter the fluids of the inner ear by diffusing across the round window membrane (RWM), the major site of absorption of medications from the middle ear into the inner ear. Unfortunately, large portions of the administered medication do not come into contact with the RWM. This portion of drug is instead absorbed by the mucosa of the middle ear or evacuated from the middle ear space by the eustachian tube. In either case, the drug is unavailable to diffuse into the inner ear. Therefore, the concentration of drug in the inner ear depends greatly upon the drug coming into contact with the RWM.

Furthermore, the treatment of diseases is a dynamic process. The medication should be discontinued when symptoms disappear or when a patient has adverse drug effects. Accordingly, there exists a need for improved compositions and methods for treating inner ear diseases.

SUMMARY OF THE INVENTION

In one aspect, compositions are provided for controlled release delivery, the compositions comprising: a chitosan glycerophosphate (CGP) hydrogel comprising at least one agent effective in the treatment of otorhinolaryngology-associated pathology (such as an inner ear disease), or Head and Neck associated pathology.

In another aspect, provided herein are methods of treating an otorhinolaryngology-associated pathology, or Head and Neck associated pathology, such as an inner ear disease, in a subject, the methods comprising the step of: administering a composition comprising a CGP hydrogel and at least one agent to a predetermined region of said subject (e.g., by applying to a round window membrane of the subject), wherein the agent is effective in the treatment of otorhinolaryngology-associated pathology (such as an inner ear disease), or Head and Neck associated pathology.

In an other aspect, provided herein are methods of treating an otorhinolaryngology and otorhinolaryngology-associated pathology, conditions, indications or their combination, or Head and Neck associated pathology conditions, indications or their combination, in a subject, the methods comprising the step of: administering a composition comprising a CGP hydrogel and at least one agent to a predetermined region of said subject (e.g., by applying to a round window membrane of the subject), wherein the agent is effective in the treatment of otorhinolaryngology and otorhinolaryngology-associated pathology, conditions, indications or to their combination, or Head and Neck associated pathology conditions, indications or their combination.

In yet another aspect, provided herein are systems for controlled release delivery, the systems comprising: (i) a chitosan glycerophosphate (CGP) hydrogel comprising at least one agent effective in the treatment of otorhinolaryngology-associated pathology (such as an inner ear disease), or Head and Neck associated pathology; and (ii) a chitosanase present in an amount effective to dissolve the CGP hydrogel and thereby release the agent associated with the CGP hydrogel.

In yet a further aspect, provided herein are methods for treating an inner ear disease, the methods comprising: (i) administering to a subject in need thereof (e.g., by applying to a round window membrane of the subject) a chitosan glycerophosphate (CGP) hydrogel comprising at least one agent effective in the treatment of an inner ear disease, and (ii) administering a chitosanase to the inner ear of the subject (e.g., by applying to the round window membrane of the subject), wherein the administration of said chitosanase dissolves the CGP hydrogel and releases the agent associated with said CGP hydrogel.

In yet a further aspect, provided herein are methods for regulating the treatment of an inner ear disease, the methods comprising: (i) administering to a subject in need thereof (e.g., by applying to a round window membrane of the subject) a chitosan glycerophosphate (CGP) hydrogel comprising at least one agent effective in the treatment of an inner ear disease, and (ii) administering a chitosanase to the inner ear of the subject (e.g., by applying to the round window membrane of the subject), wherein the administration of said chitosanase dissolves the CGP hydrogel and releases the agent associated with said CGP hydrogel.

In an additional aspect, provided herein are methods for alleviating a drug induced ototoxicity or adverse effect, the method comprising: administering a chitosanase to an inner ear of a subject (e.g., by applying to a round window membrane of the subject) having a CGP hydrogel based drug delivery composition applied to said inner ear, wherein the administration of said chitosanase dissolves said CGP hydrogel and releases said drug associated with said CGP hydrogel, thereby alleviating said drug induced ototoxicity or adverse effect.

In yet an additional aspect, the invention provides are methods for regulating a drug release from a CGP hydrogel based drug delivery composition in an inner ear of a subject (e.g., by applying to a round window membrane of the subject) having said drug delivery composition applied to said inner ear, the methods comprising: administering a chitosanase to said inner ear of said subject, wherein administration of said chitosanase dissolves the CGP hydrogel to release a drug associated with the CGP hydrogel, thereby regulating said drug release from the CGP hydrogel in the inner ear of the subject.

In yet an other aspect, provided herein are methods for removing a drug from a CGP hydrogel based drug delivery composition applied to an inner ear of a subject, the methods comprising: administering a chitosanase to said inner ear of said subject (e.g., by applying to a round window membrane of the subject), wherein the administration of said chitosanase dissolves said CGP hydrogel and releases said drug associated with said CGP hydrogel, thereby removing said drug from said CGP hydrogel based drug delivery system applied to said inner ear of said subject.

Unless otherwise defined, all technical and scientific terms used herein have the same meaning as commonly understood by one of ordinary skill in the art to which this invention belongs. Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description. It is also contemplated that whenever appropriate, any embodiment of the present invention can be combined with one or more other embodiments of the present invention, even though the embodiments are described under different aspects of the present invention.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE INVENTION

Figure 1:
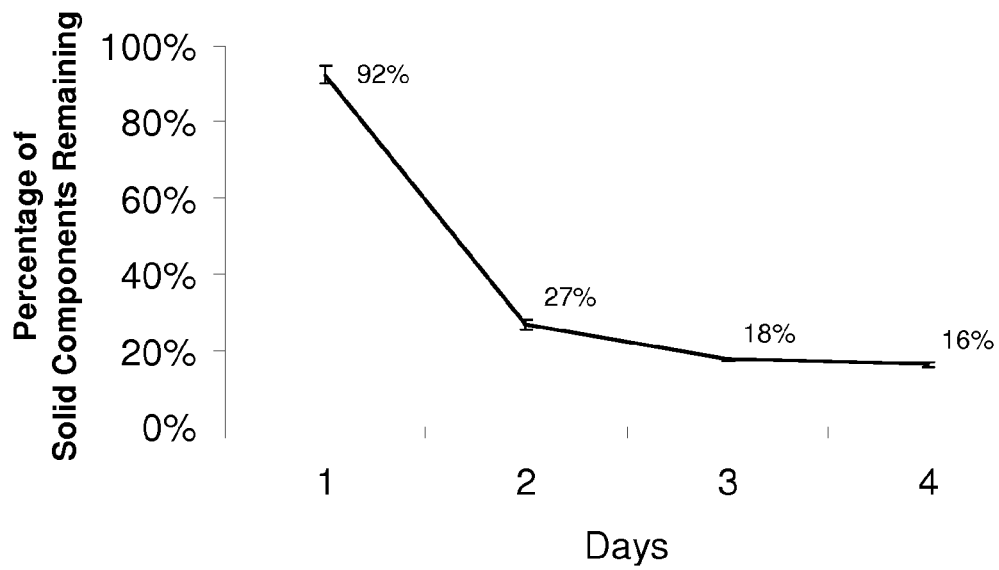
FIG. 1 shows how CGP-Dex-Hydrogel degrades in a controlled Manner. 16% of solid CGP-Dex-hydrogel remains after 4 days. The degradation of CGP-Dex-hydrogel is controlled and is tapered. The error bars represent the SEM (±0.002 to 0.026).

The invention relates to a controlled release delivery compositions and methods of using them for pathologies associated with Otorhinolaryngology and Head and Neck.

The invention relates, in one embodiment, to a controlled release delivery composition for otorhinolaryngology and otorhinolaryngology-associated pathology, conditions, indications or their combination, Head and Neck associated pathology conditions, indications or their combination, or their combination, comprising a chitosan-glycerophosphate (CGP) hydrogel and an agent, bio-materials and their combination. The invention also relates, in another embodiment, to a composition comprising a chitosanase that hydrolyses or dissolves the CGP hydrogel in order to regulate the release of a drug associated with the CGP hydrogel. In another embodiment, a composition as described herein delivers an agent at a controlled rate for an extended time. In another embodiment, the composition is localized by spatial placement near where it is needed. In another embodiment, the composition targets a drug action by using techniques known to a person of skill in the art. In another embodiment, targeting comprises delivery of a drug to a particular organ. In another embodiment, targeting comprises delivery of a drug to a particular tissue. In another embodiment, targeting comprises delivery of a drug to a particular cell type. In one embodiment, the compositions provided herein comprise a CGP hydrogel having a first chitosan to glycerophosphate ratio; and a CGP hydrogel having a second chitosan to glycerophosphate ratio, wherein the first chitosan to glycerophosphate ratio is different from the second chitosan to glycerophosphate ratio; and one or more additional agent. In one embodiment, the additional agent is a bio-material, as described hereinbelow.

In one aspect, compositions are provided for controlled release delivery, the compositions comprising: a chitosan glycerophosphate (CGP) hydrogel comprising at least one agent effective in the treatment of otorhinolaryngology-associated pathology (such as an inner ear disease), or Head and Neck associated pathology.

In another aspect, provided herein are methods of treating an otorhinolaryngology-associated pathology, or Head and Neck associated pathology, such as an inner ear disease, in a subject, the methods comprising the step of: administering a composition comprising a CGP hydrogel and at least one agent to a predetermined region of said subject (e.g., by applying to a round window membrane of the subject), wherein the agent is effective in the treatment of otorhinolaryngology-associated pathology (such as an inner ear disease), or Head and Neck associated pathology.

In an other aspect, provided herein are methods of treating an otorhinolaryngology and otorhinolaryngology-associated pathology, conditions, indications or their combination, or Head and Neck associated pathology conditions, indications or their combination, in a subject, the methods comprising the step of: administering a composition comprising a CGP hydrogel and at least one agent to a predetermined region of said subject (e.g., by applying to a round window membrane of the subject), wherein the agent is effective in the treatment of otorhinolaryngology and otorhinolaryngology-associated pathology, conditions, indications or their combination, or Head and Neck associated pathology conditions, indications or their combination.

In yet another aspect, provided herein are systems for controlled release delivery, the systems comprising: (i) a chitosan glycerophosphate (CGP) hydrogel comprising at least one agent effective in the treatment of otorhinolaryngology-associated pathology (such as an inner ear disease), or Head and Neck associated pathology; and (ii) a chitosanase present in an amount effective to dissolve the CGP hydrogel and thereby release the agent associated with the CGP hydrogel.

In yet a further aspect, provided herein are methods for treating an inner ear disease, the methods comprising: (i) administering to a subject in need thereof (e.g., by applying to a round window membrane of the subject) a chitosan glycerophosphate (CGP) hydrogel comprising at least one agent effective in the treatment of an inner ear disease, and (ii) administering a chitosanase to the inner ear of the subject (e.g., by applying to the round window membrane of the subject), wherein the administration of said chitosanase dissolves the CGP hydrogel and releases the agent associated with said CGP hydrogel.

In yet a further aspect, provided herein are methods for regulating the treatment of an inner ear disease, the methods comprising: (i) administering to a subject in need thereof (e.g., by applying to a round window membrane of the subject) a chitosan glycerophosphate (CGP) hydrogel comprising at least one agent effective in the treatment of an inner ear disease, and (ii) administering a chitosanase to the inner ear of the subject (e.g., by applying to the round window membrane of the subject), wherein the administration of said chitosanase dissolves the CGP hydrogel and releases the agent associated with said CGP hydrogel.

In an additional aspect, provided herein are methods for alleviating a drug induced ototoxicity or adverse effect, the method comprising: administering a chitosanase to an inner ear of a subject (e.g., by applying to a round window membrane of the subject) having a CGP hydrogel based drug delivery composition applied to said inner ear, wherein the administration of said chitosanase dissolves said CGP hydrogel and releases said drug associated with said CGP hydrogel, thereby alleviating said drug induced ototoxicity or adverse effect.

In yet an additional aspect, the invention provides are methods for regulating a drug release from a CGP hydrogel based drug delivery composition in an inner ear of a subject (e.g., by applying to a round window membrane of the subject) having said drug delivery composition applied to said inner ear, the methods comprising: administering a chitosanase to said inner ear of said subject, wherein administration of said chitosanase dissolves the CGP hydrogel to release a drug associated with the CGP hydrogel, thereby regulating said drug release from the CGP hydrogel in the inner ear of the subject.

In yet an other aspect, provided herein are methods for removing a drug from a CGP hydrogel based drug delivery composition applied to an inner ear of a subject, the methods comprising: administering a chitosanase to said inner ear of said subject (e.g., by applying to a round window membrane of the subject), wherein the administration of said chitosanase dissolves said CGP hydrogel and releases said drug associated with said CGP hydrogel, thereby removing said drug from said CGP hydrogel based drug delivery system applied to said inner ear of said subject.

In another embodiment, the CGP hydrogel controls entry to the body according to the specifications of the required drug delivery profile. In another embodiment, the CGP hydrogel controls the rate and duration of delivery. In another embodiment, the rate and duration of delivery are designed to achieve the desired concentration. In another embodiment, the CGP hydrogel is a sustained release composition.

In another embodiment, the CGP hydrogel of the invention reduces side effects because effective concentration of a drug is maintained. In another embodiment, the CGP hydrogel of the invention eliminates damage to non-target.

In another embodiment, the CGP hydrogel serves as a drug reservoir. In another embodiment, the drug diffuses from the CGP hydrogel. In another embodiment, the CGP hydrogel comprising a drug of the invention is placed near or at the site of treatment.

In another embodiment, the drug is physically blended with the CGP hydrogel. In another embodiment, the drug is dissolved or dispersed within the chitosan-glycerophosphate (CGP) hydrogel. In another embodiment, the drug is uniformly dissolved or dispersed within the chitosan-glycerophosphate (CGP) hydrogel. In another embodiment, the characteristics of the CGP hydrogel define a drug rate-controlling mechanism.

In addition, the CGP hydrogels of the invention may be incorporated into sustained-release, pulsed release, controlled release or postponed release preparations and formulations.

Controlled or sustained release compositions include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

In one embodiment, the composition can be delivered in a controlled release system. For example, the agent may be administered using intravenous infusion, an implantable osmotic pump, a transdermal patch, liposomes, or other modes of administration. In one embodiment, a pump may be used (see Langer, infra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used. In another embodiment, a controlled release system can be placed in proximity to the therapeutic target, i.e., the ear nose or throat, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249: 1527-1533 (1990).

In another embodiment, the CGP hydrogel comprises a microbead structure. In another embodiment, the CGP hydrogel comprises a microtube structure or a polymeric hollow fiber. In another embodiment, the CGP hydrogel serves as an osmotic pump.

In another embodiment, the CGP hydrogel is further surrounded by a polymer film that further controls the drug release rate. In another embodiment, the CGP hydrogel serves as a drug reservoir implant. In another embodiment, the CGP hydrogel comprises a rate control mechanism of solvent activation. In another embodiment, the CGP hydrogel absorbs fluids. In another embodiment, the CGP hydrogel is swollen. In another embodiment, swelling allows drug to migrate more easily. In another embodiment, water penetrates the CGP hydrogel thus forming pores and releasing the drug.

In another embodiment, a CGP hydrogel releases a drug over a period of 2-4 hours. In another embodiment, a CGP hydrogel releases a drug over a period of 3-9 hours. In another embodiment, a CGP hydrogel releases a drug over a period of 5-15 hours. In another embodiment, a CGP hydrogel releases a drug over a period of 10-20 hours. In another embodiment, a CGP hydrogel releases a drug over a period of 15-30 hours. In another embodiment, a CGP hydrogel releases a drug over a period of 25-40 hours. In another embodiment, a CGP hydrogel releases a drug over a period of 30-45 hours. In another embodiment, a CGP hydrogel releases a drug over a period of 45-60 hours. In another embodiment, a CGP hydrogel releases a drug over a period of 50-70 hours. In another embodiment, a CGP hydrogel releases a drug over a period of 60-90 hours. In another embodiment, a CGP hydrogel releases a drug over a period of 90-120 hours.

In another embodiment, a CGP hydrogel releases a drug over a period of 5-7 days. In another embodiment, a CGP hydrogel releases a drug over a period of 6-10 days. In another embodiment, a CGP hydrogel releases a drug over a period of 10-15 days. In another embodiment, a CGP hydrogel releases a drug over a period of 15-20 days. In another embodiment, a CGP hydrogel releases a drug over a period of 20-30 days. In another embodiment, a CGP hydrogel releases a drug over a period of 30-45 days. In another embodiment, a CGP hydrogel releases a drug over a period of 45-90 days. In another embodiment, a CGP hydrogel releases a drug over a period of 90-120 days. In another embodiment, a CGP hydrogel releases a drug over a period of 100-200 days. In another embodiment, a CGP hydrogel releases a drug over a period of 200-370 days.

In another embodiment, a CGP hydrogel releases a drug over a period of 1-1.5 years. In another embodiment, a CGP hydrogel releases a drug over a period of 1-2 years. In another embodiment, a CGP hydrogel releases a drug over a period of 1.5-3 years.

CGP hydrogel compositions described herein may comprise a drug or a bioactive agent. In some embodiments, the CGP hydrogel compositions described herein treat an Otorhinolaryngology-associated pathologies. In some embodiments, the CGP hydrogel compositions described herein treat Head and Neck associated pathologies. In some embodiments, the CGP hydrogel compositions described herein prevent an Otorhinolaryngology-associated pathology, Head and Neck associated pathology or their combination. In some embodiments, the CGP hydrogel compositions described herein inhibit an Otorhinolaryngology-associated pathology, Head and Neck associated pathology or their combination. In some embodiments, the CGP hydrogel compositions described herein improve the condition of a patient affected with an Otorhinolaryngology-associated pathology, Head and Neck associated pathology or their combination.

In some embodiments, the Otorhinolaryngology-associated pathology is hearing loss. In some embodiments, the Otorhinolaryngology-associated pathology is vertigo. In some embodiments, the Otorhinolaryngology-associated pathology is a vestibular Disorder. In some embodiments, the Otorhinolaryngology-associated pathology is an ear infection. In some embodiments, the Otorhinolaryngology-associated pathology is Otitis Media. In some embodiments, the Otorhinolaryngology-associated pathology is a sinus infections or a sinus disease. In some embodiments, the Otorhinolaryngology-associated pathology is scaring or stenosis of openings within the ear and sinuses. In some embodiments, the Otorhinolaryngology-associated pathology is a cancer associated with the head and neck. In some embodiments, the Otorhinolaryngology-associated pathology comprises an abscess or an infections of the ear, nose, throat, head, neck, or a combination thereof. In some embodiments, the Otorhinolaryngology-associated pathology comprises otology pathology. In some embodiments, the Otorhinolaryngology-associated pathology comprises neurotology pathology. In some embodiments, the Otorhinolaryngology-associated pathology comprises rhinology pathology. In some embodiments, the Otorhinolaryngology-associated pathology comprises an allergy. In some embodiments, the Otorhinolaryngology-associated pathology comprises laryngology pathology. In some embodiments, the Otorhinolaryngology-associated pathology comprises bronchoesophagology pathology.

In one embodiment, Head and Neck associated pathology is Branchial Cleft Cyst. Or in another embodiment, the Head and Neck associated pathology is a salivary-gland associated pathology, a thyroid-associated pathology, Verrucal Keratosis of the larynx or their combination in certain other embodiment. Head and Neck-associated pathology, refers to any pathology associated with the head, neck or organs or tissue comprised in the head and neck.

The terms "active pharmaceutical ingredient", "agent", and "drug" are used interchangeably here. In one embodiment, the agent is a steroid. In one embodiment, the agent is an antibiotic agent. In one embodiment, the agent is an antiviral agent. In one embodiment, the agent is a fungicidal. In one embodiment, the agent is a neurological agent. In one embodiment, the agent is non-steroidal anti-inflammatory agent.

In another embodiment, the agent is dexamethasone. In another embodiment, the agent is acetic acid. In another embodiment, the agent is acetic acid-aluminum acetate. In another embodiment, the agent is hydrocortisone. In another embodiment, the agent is hydrocortisone-acetic acid. In another embodiment, the agent is benzocaine. In another embodiment, the agent is benzotic. In another embodiment, the agent is floxin. In another embodiment, the agent is ciprodex. In another embodiment, the agent is cipro. In another embodiment, the agent is flunisolide. In another embodiment, the agent is fluticasone. In another embodiment, the agent is mometasone. In another embodiment, the agent is ipratropium. In another embodiment, the agent is beconase. In another embodiment, the agent is triamcinolone. In another embodiment, the agent is chlorhexidine gluconate. In another embodiment, the agent is doxycycline. In another embodiment, the agent is pilocarpine. In another embodiment, the agent is levocabastine. In another embodiment, the agent is sodium cromoglycate. In another embodiment, the agent is bacitracin zinc. In another embodiment, the agent is polymyxin B-sulfate. In another embodiment, the agent is chloramphenicol. In another embodiment, the agent is erythromycin.

In another embodiment, the agent is levocabastine HCl. In another embodiment, the agent is ciprofloxacin HCl. In another embodiment, the agent is ciprofloxacin HCl/hydrocortisone. In another embodiment, the agent is gentamycin. In another embodiment, the agent is erythromycin. In another embodiment, the agent is framycetin sulfate. In another embodiment, the agent is gramicidin. In another embodiment, the agent is gentamicin sulfate. In another embodiment, the agent is gramicidin. In another embodiment, the agent is neomycin sulfate. In another embodiment, the agent is ofloxacin. In another embodiment, the agent is trimethoprim sulfate. In another embodiment, the agent is sulfacetamide sodium. In another embodiment, the agent is tobramycin trifluridine. In another embodiment, the agent is beclomethasone dipropionate. In another embodiment, the agent is betamethasone sodium phosphate. In another embodiment, the agent is budesonide. In another embodiment, the agent is clioquinol. In another embodiment, the agent is fluorometholone. In another embodiment, the agent is fluorometholone acetate. In another embodiment, the agent is prednisolone acetate. In another embodiment, the agent is triamcinolone acetonide. In another embodiment, the agent is diclofenac sodium. In another embodiment, the agent is flurbiprofen sodium. In another embodiment, the agent is atropine sulfate. In another embodiment, the agent is cyclopentolate HCl. In another embodiment, the agent is dipivefrin HCl. In another embodiment, the agent is homatropine Hbr. In another embodiment, the agent is benzydamine HCl. In another embodiment, the agent is antazoline phosphate. In another embodiment, the agent is naphazoline HCl. In another embodiment, the agent is phenylephrine HCl. In another embodiment, the agent is brimonidine tartrate. In another embodiment, the agent is timolol maleate. In another embodiment, the agent is betaxolol HCl. In another embodiment, the agent is dipivefrin HCl. In another embodiment, the agent is levobunolol HCl. In another embodiment, the agent is acetazolamide brinzolamide. In another embodiment, the agent is dorzolamide HCl. In another embodiment, the agent is carbachol. In another embodiment, the agent is pilocarpine HCl. In another embodiment, the agent is bimatoprost. In another embodiment, the agent is latanoprost. In another embodiment, the agent is travoprost. In another embodiment, the agent is apraclonidine HCl.

In another embodiment, the agent is an adrenocorticoid such as but not limited to betamethasone, cortisone, dexamethasone, hydrocortisone, methylprednisolone, paramethasone, prednisolone, prednisone, and triamcinolone. Exemplary analgesics include acetaminophen, aspirin, buprenorphine, butalbital, butorphanol, codeine, dezocine, diflunisal, dihydrocodeine, etodolac, fenoprefen, fentanyl, floctafenine, hydrocodone, hydromorphone, ibuprofen, ketoprofen, ketorolac, levorphanol, magnesium salicylate, meclofenamate, mefenamic acid, meperidine, meprobamate, methadone, methotrimeprazine, morphine, nalbuphine, naproxen, opium, oxycodone, oxymorphone, pentazocine, phenobarbital, propoxyphene, salsalate, and sodium salicylate. One exemplary analgesic adjunct is caffeine. Exemplary anesthetics include articane-epinephrine, bupivacaine, chloroprocaine, etidocaine, ketamine, lidocaine, mepivacaine, methohexital, prilocaine, propofol, propoxycaine, tetracaine, and thiopental. One exemplary analgesic-anesthetic is antipyrine-benzocaine.

In another embodiment, the agent is an antibiotic such as but not limited to anti-bacterials, and anti-infectives include sulfonamides (e.g., sulfanilamide, sulfadiazine, sulfamethoxazole, sulfisoxazole, para-aminobenzoic acid, or sulfacetamide), trimethoprim-sulfamethoxazole, quinolones (e.g., ciprofloxacin, ofloxacin, or nalidixic acid), .beta.-lactam antibiotics such as penicillins or cephalosporins, aminoglycosides (e.g., kanamycin, tobromycin, gentamycin C, amikacin, neomycin, netilmicin, streptomycin, or vancomycin), tetracyclines, chloramphenicol, and macrolides (e.g., erythromycin, clarithromycin, or azithromycin). Non-limiting examples of suitable penicillins include penicillin G, penicillin V, methicillin, oxacillin, nafeillin, ampicillin, and amoxicillin Non-limiting examples of suitable cephalosporins include cephalothin, cefdinir, cefozolin, cephalexin, cefadraxal, cefamandole, cefoxitin, cefaclor, cefonicid, cefoletan, cefotaxime, ceftizoxime, cefrtriaxone, cefditoren, and cefepine. Exemplary antibiotics useful for treating OM include penicillins such as amoxicillin and amoxicillin-clavulanate (Augmentin®); sulfa-based combinations such as erythromycin-sulfisoxazole (Pediazole), trimethoprim-sulfamethoxazole (Bactrim, Septra°); macrolides/azalides such as azithromycin (Zithromax®) or clarithromycin (Biaxin®); second-generation cephalosporins such as cefaclor (Ceclor®), cefprozil (Cefzil®), cefuroxime axetil (Ceftin®), or loracarbef (Lorabid®); and third generation cephalosporins such as cefdinir (Omnicef®), cefixime (Suprax®), cefpodoxime proxetil (Vantin®), ceftibuten (Cedax®), cefditoren (Spectracef,®), and ceftriaxone (Rocephin®).

In another embodiment, the agent is an anti-emetic such as but not limited to buclizine, chlorpromazine, cyclizine, dimenhydrinate, diphenhydramine, diphenidol, domperidone, dronabinol, haloperidol, hydroxyzine, meclizine, metoclopramine, nabilone, ondansetron, perphenazine, prochlorperazine, promethazine, scopolamine, thiethylperazine, triflupromazine, and trimethobenzamine. Exemplary antifungals include amphotericin B, clioquinol, clotrimazole, fluconazole, flucytosine, griseofulvin, ketoconazole, miconazole, and potassium iodide. Exemplary anti-inflammatory agents include aluminum acetate, aspirin, betamethasone, bufexamac, celecoxib, dexamethasone, diclofenac, etodolac, flurbiprofen, hydrocortisone, indomethacin, magnesium salicylate, naproxen, prednisolone, rofecoxib, salsalate, sulindac, and triamcinolone. Exemplary anti-vertigo agents suitable for the invention include belladonna, dimenhydrinate, diphenhydramine, diphenidol, meclizine, promethazine, and scopolamine. Exemplary anti-viral agents suitable for the invention include acyclovir, amantadine, delavirdine, didanosine, efavirenz, foscamet, ganciclovir, indinavir, nelfinavir, ribavirin, ritonavir, zalcitabine, and zidovudine. Exemplary biological response modifiers include aldesleukin, interferon α-2a, interferon α-2b, interferon α-n1, interferon α-n3, interferon γ, and levamisole. Exemplary cytotoxic agents include podofilox and podophyllum. Exemplary immunizing agents include influenza virus vaccine, pneumococcal vaccine polyvalent, and immune globulin. An exemplary immunomodulator invention is interferon γ. Other pharmacologic agents suitable for the invention include betahistine (e.g., for treating the nausea, dizziness, and ringing in the ears that occur in Ménière's disease), prochlorperazine, and hyoscine.

In another embodiment, the agent is chlorhexidine gluconate.

In another embodiment, the composition comprises 0.5-40% (w/w) chitosan. In another embodiment, the composition comprises 1-5% (w/w) chitosan. In another embodiment, the composition comprises 2-8% (w/w) chitosan. In another embodiment, the composition comprises 5-10% (w/w) chitosan. In another embodiment, the composition comprises 8-12% (w/w) chitosan. In another embodiment, the composition comprises 12-20% (w/w) chitosan. In another embodiment, the composition comprises 15-25% (w/w) chitosan. In another embodiment, the composition comprises 20-30% (w/w) chitosan. In another embodiment, the composition comprises 25-35% (w/w) chitosan. In another embodiment, the composition comprises 30-40% (w/w) chitosan.

In another embodiment, the composition comprises 1-60% (w/w) glycerophosphate. In another embodiment, the composition comprises 1-5% (w/w) glycerophosphate. In another embodiment, the composition comprises 5-15% (w/w) glycerophosphate. In another embodiment, the composition comprises 10-20% (w/w) glycerophosphate. In another embodiment, the composition comprises 15-25% (w/w) glycerophosphate. In another embodiment, the composition comprises 20-30% (w/w) glycerophosphate. In another embodiment, the composition comprises 25-35% (w/w) glycerophosphate. In another embodiment, the composition comprises 35-45% (w/w) glycerophosphate. In another embodiment, the composition comprises 40-50% (w/w) glycerophosphate. In another embodiment, the composition comprises 50-60% (w/w) glycerophosphate.

In another embodiment, the composition is in a solid form. In another embodiment, the composition is in a liquid form. In another embodiment, the composition is in a gel form. In another embodiment, the composition is in a semi-gel form. In another embodiment, the composition's form is determined by factors comprising the ratio of glycerophosphate to chitosan. In another embodiment, the agent release profile is determined by factors comprising the ratio of glycerophosphate to chitosan. In another embodiment, the higher the ratio of chitosan to glycerophosphate when the agent is hydrophilic, the longer is the agent release following the initial release. In another embodiment, the lower the ratio of chitosan to glycerophosphate when the agent is hydrophobic, the longer is the agent release following the initial release.

In another embodiment, by altering the composition of CGP-hydrogel the physical properties can be adjusted to fit various release strategies. In another embodiment, these properties comprise the diameter of pores in the matrix, the strength of the matrix and the rate of matrix degradation. In another embodiment, by altering the pore size, the initial volume of drug released is controlled as a bolus early in the treatment course. In another embodiment, the mechanical strength of the CGP-hydrogel is fortified by adjusting the proportions of the hydrogel components permitting the design of hydrogels with reduced susceptibility to degradation, thereby prolonging the release of drug. In another embodiment, susceptibility of CGP-hydrogel to degradation by lysozyme is also adjustable which further enables fine tuning of the drug release properties of this system for the specific requirements of a given clinical scenario.

In another embodiment, the composition comprises at least two different chitosan to glycerophosphate ratios. In another embodiment, the composition comprises two different chitosan to glycerophosphate ratios. In another embodiment, the composition comprises three different chitosan to glycerophosphate ratios. In another embodiment, the composition comprises four different chitosan to glycerophosphate ratios. In another embodiment, the composition comprises five different chitosan to glycerophosphate ratios. In another embodiment, the composition comprises six different chitosan to glycerophosphate ratios.

In another embodiment, the invention provides a method of treating an Otorhinolaryngology-associated pathology in a subject, comprising the step of administering a composition comprising a CGP hydrogel and an agent, bio-materials and their combination in a predetermined region in a subject (e.g., within the ear of the subject). In another embodiment, the method comprises trans-tympanic administration. In another embodiment, the method comprises intra-tympanic administration. In another embodiment, the method comprises intra-mascular administration. In another embodiment, the method comprises intra-ear administration. In another embodiment, the method comprises administration into the Round Window Niche (RWN). Bio-material refers to any material in addition to the active pharmaceutical ingredient (API) or the agent used in the methods and compositions described herein, which is beneficial in the treatment of Otorhinolaryngology-associated pathology in a subject, such as an abscess in one embodiment or infections of the ear, nose, throat, head, neck, or a combination thereof in other discrete embodiments. In another embodiment, the bio-material is antibiotics, or anti-virals, antifungals, anesthetics, anti-inflammatory agents, anti-allergic agents, penetration enhancement agents, wetting agents, surface active agents, diluents, viscosity enhancing agents, chemotherapeutic agents, or their combination in other discrete embodiments of the biomaterials used in the controlled release compositions described herein.

In another embodiment, the method comprises administering the composition of the invention in a solid state. In another embodiment, the method comprises administering the composition of the invention in a liquid state. In another embodiment, the method comprises administering the composition of the invention in a gel form. In another embodiment, the invention provides that the composition's states of aggregation changes from a liquid to a semi-solid gel when maintained in a temperature of 36° C. to 38° C. In another embodiment, the method comprises administering the composition in a semi-solid gel form. In another embodiment, the method provides that a semi-solid gel form is preserved in a subject's body temperature.

In another embodiment, the hydrogel further comprises macromolecular or polymeric materials into which water and small molecules can easily diffuse and include hydrogels prepared through cross-linking. Cross-linking may be either through covalent, ionic or hydrophobic bonds introduced through use of either chemical cross-linking agents or electromagnetic radiation, such as ultraviolet light, of both natural and synthetic hydrophilic polymers, including homo and co-polymers. In another embodiment, additional hydrogels of interest include those prepared through the cross-linking of: polyethers, e.g. polyakyleneoxides such as poly(ethylene glycol), poly(ethylene oxide), poly(ethylene oxide)-co-(poly (propyleneoxide) block copolymers; poly(vinyl alcohol); poly(vinyl pyrrolidone); polysaccharides, e.g. hyaluronic acid, dextran, chondroitin sulfate, heparin, heparin sulfate or alginate; proteins, e.g. gelatin, collagen, albumin, ovalbumin or polyamino acids; and the like.

In another embodiment, the physical characteristics such as size, shape and surface area can affect the absorption and release characteristics of the hydrogel composition. In another embodiment, the hydrogel composition that is employed may be in a variety of configurations, including particles, beads, rods, sheets, irregular shapes and the like. In another embodiment, the hydrogel shape comprises greater surface area to total mass ratios. In another embodiment, the porosity of the hydrogel affects the absorption and release characteristics of the hydrogel.

In another embodiment, the amount of pharmacologic agent present in the composition is dependent on the type of pharmacologic agent and its known effective dosage. In another embodiment, as described hereinabove a composition can include any type of pharmacologic agent, including, e.g., an adrenocorticoid (corticosteroid, steroid), analgesic, analgesic adjunct, analgesic-anesthetic, anesthetic, antibiotic, antibacterial, anti-infective, antibiotic therapy adjunct, antidote, anti-emetic, anti-fungal, antiinflammatory, anti-vertigo, anti-viral, biological response modifier, cytotoxic, diagnostic aid, immunizing agent, immunomodulator, proteins, peptides, and other agents that may useful in treating ear disorders. Analgesic, analgesic adjunct, analgesic-anesthetic, anesthetic, antibiotic, antibacterial, anti-infective, antibiotic therapy adjunct, anti-fungal, anti-inflammatory, anti-viral, and peptides are particularly useful.

In another embodiment, a composition of the invention can include a plurality of pharmacologic agents, including two or more agents within the same class (e.g., two different antibiotics) or two or more agents of various types, depending on the effect desired. For example, to fight a bacterial infection, to reduce tissue inflammation, and to alleviate irritation, a composition can contain an antibacterial, an anti-inflammatory, and an anesthetic or analgesic. In another embodiment, those skilled in the art can identify pharmacologic agents and combine them as needed to achieve a desired effect.

To further tailor the binding properties of the hydrogel, in another embodiment, the hydrogel can be modified to provide for specific binding of one or more of the agents to the surface of the hydrogel. In another embodiment, the hydrogel comprises agents that act as water absorbents and/or precipitants, where such agents include ethanol, PEG 400, phosphate buffer and the like.

It will be appreciated that the hydrogel compositions employed in the subject methods can be prepared by methods known to those skilled in the art.

The invention also provides a pharmaceutical composition comprising small molecule, antibody, nucleic acid, peptide, vector, host cell, or other agents of this invention and one or more pharmaceutically acceptable carriers. "Pharmaceutically acceptable carriers" include any excipient which is non-toxic to the cell or mammal being exposed thereto at the dosages and concentrations employed. The pharmaceutical composition may include one or additional therapeutic agents.

Pharmaceutically acceptable carriers include solvents, dispersion media, buffers, coatings, antibacterial and antifungal agents, wetting agents, preservatives, buggers, chelating agents, antioxidants, isotonic agents and absorption delaying agents.

Pharmaceutically acceptable carriers include water; saline; phosphate buffered saline; dextrose; glycerol; alcohols such as ethanol and isopropanol; phosphate, citrate and other organic acids; ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; EDTA; salt forming counterions such as sodium; and/or nonionic surfactants such as TWEEN, polyethylene glycol (PEG), and PLURONICS; isotonic agents such as sugars, polyalcohols such as mannitol and sorbitol, and sodium chloride; as well as combinations thereof. Antibacterial and antifungal agents include parabens, chlorobutanol, phenol, ascorbic acid, and thimerosal.

Figure 5:
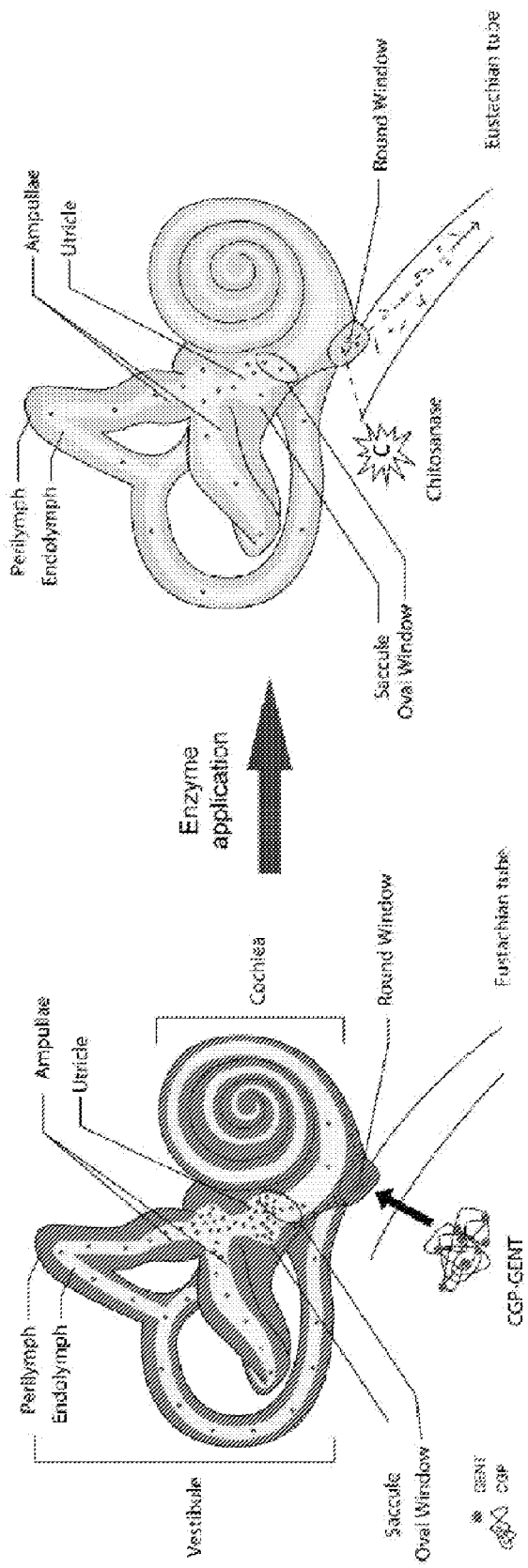
FIG. 5. Regulated CGP hydrogel drug delivery system. A chitosan-glycerophosphate-gentamicin (CGP-GENT) hydrogel was applied to the RWM (Left), resulting in a steady release of the drug into the perilymph, and a vestibular-dominant distribution (represented as dots in the ampullae, utricle, and saccule organs). Chitosanase enzyme was applied after 24 h to digest the hydrogel (Right), thus decreasing the gentamicin levels (represented as pale and decreased number of dots).

Another aspect of the invention is a chitosanase containing composition in which the chitosanase is present in an amount effective to dissolve a CGP hydrogel and thereby release a drug in the CGP hydrogel. If a patient has a CGP hydrogel composition applied to an inner ear and the drug present in the CGP hydrogel exhibits an ototoxicity or an adverse effect, then a chitosanase containing composition can be administered to patient's inner ear. The chitosanase can hydrolyse or dissolve the CGP hydrogel and thereby release the drug in the CGP hydrogel. The released drug can then be removed from patient's inner ear through the Eustachian tube and into the nasopharynx (See FIG. 5), thus limiting its ability to continue to enter the inner ear in order to reduce or treat for the ototoxicity or adverse effect. Additionally, if a patient has a CGP hydrogel composition applied to an inner ear and the patient has been successfully treated or at least one symptom has been alleviated, then a chitosanase containing composition can be administered to patient's inner ear. The released drug can then be removed from patient's inner ear through the Eustachian tube and into the nasopharynx (See FIG. 5), thus stopping or reducing treatment by the drug.

In one embodiment, the chitosanase present in the composition can be used to regulate the release of a drug present in a CGP hydrogel composition. In some embodiments, the chitosanase containing composition may also include another agent (e.g., a therapeutic agent or drug).

In some embodiments, the amount of chitosanase present in the systems and used in the methods described herein is sufficient to release from the hydrogel at least about 10% of the drug, by at least about 20% of the drug, by at least about 25% of the drug, by at least about 30% of the drug, by at least about 40% of the drug, by at least about 50% of the drug, by at least about 60% of the drug, by at least about 70% of the drug, by at least about 75% of the drug, by at least about 80% of the drug, by at least about 90% of the drug, by at least about 95% of the drug, by at least about 98% of the drug, or by about 99% or more of the drug.

In some embodiments, the amount of chitosanase present in the systems and used in the methods described herein releases one of the foregoing percentages of the drug within a period of no more than about two days, about 36 hours, about 24 hours, about 20 hours, about 18 hours, about 15 hours, about 12 hours, about 10 hours, about 8 hours, about 6 hours, about 3 hours, about 2 hours, about 1 hour or less.

The chitosanase containing composition may be formulated in a variety of ways such that it is in a form suitable for administration to the ear of the subject. The composition may be formulated as an immediate, controlled, extended or delayed release composition. In some embodiments, the compositions are in the form of injectable or infusible solutions.

The chitosanase containing compositions suitable for use should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences, Mack Publishing Co., 16th ed. (1980). Suitable carriers, additives, adjuvants, mode of delivery, route of delivery, therapeutic agents, and treatment methods described herein with respect to the CGP hydrogel containing composition can also be used in a chitosanase containing composition described herein. One of skilled in the art can readily determine the suitability depending on a need.

In some embodiments, the compositions of the invention may include isotonic agents, for example, sugars, polyalcohols, such as mannitol, sorbitol, or sodium chloride.

Sterile compositions can be prepared by filtered sterilization. Generally, dispersions are prepared by incorporating the active compound into a sterile vehicle, which contains a basic dispersion medium and the required other ingredients from those enumerated above. The preparations may be packaged and sold in the form of a kit such as those described in US Appl. Publ. No. 2002/0102208 A1, which is incorporated herein by reference in its entirety. Such articles of manufacture will preferably have labels or package inserts indicating that the associated compositions are useful for treating a subject suffering from ear disease or disorders.

As used herein, an "effective amount" refers to an amount effective, at dosages and for periods of time necessary, to achieve the desired result. A therapeutically effective amount of a molecule may vary according to factors such as the disease state, age, sex, and weight of the individual, and the ability of the molecule to elicit a desired response in the individual. A therapeutically effective amount is also one in which any toxic or detrimental effects of the molecule are outweighed by the therapeutically beneficial effects. It will be appreciated that the selection of an effective amount or a therapeutically effective amount in a particular instance will be within the discretion of a person skilled in the art.

The invention further provides a kit comprising a CGP hydrogel containing composition or a chitosanase containing composition or both.

The invention also provides an implant, a formulation, or a drug delivery system comprising a CGP hydrogel containing composition or a chitosanase containing composition or both. In some embodiments, the invention provides an implant, a formulation, or a drug delivery system comprising a first composition that comprises the CGP hydrogel in combination with a drug and second composition that comprises a chitosanase. In particular embodiments, provided herein are implants, formulations, or systems for drug delivery comprising a combination of both CGP hydrogel containing composition and chitosanase containing composition, where the chitosanase can be used to regulate the release of a drug present in the CGP hydrogel containing composition. Based on a desired release rate or release duration of a drug, one of skilled in the art can design the chitosanase release by adding suitable additives to the chitosanase containing composition.

A CGP hydrogel containing composition or a chitosanase containing composition may be administered alone, or in combination with one or more other therapeutically effective agents. In one embodiment, a CGP hydrogel containing composition may be administered alone, or in combination with one or more therapeutically effective agents or treatments. In another embodiment, a chitosanase containing composition may be administered alone, or in combination with one or more therapeutically effective agents or treatments. The other therapeutically effective agent or treatment may be administered prior to, during and/or after the administration of CGP hydrogel containing composition and/or chitosanase containing composition.

In one embodiment, a CGP hydrogel containing composition is co-administered with a chitosanase containing composition, and thereby the chitosanase can regulate the release of a drug present in the CGP hydrogel containing composition. In another embodiment, a CGP hydrogel containing composition is administered independently from the administration of a chitosanase containing composition. In some embodiments, a chitosanase containing composition is administered to dissolve the CGP hydrogel, and thereby remove the drug present in the CGP hydrogel so as to stop the drug administration or the decrease the drug induced ototoxicities or adverse effects.

The administration of the CGP hydrogel containing composition and/or chitosanase containing composition with other agents and/or treatments may occur simultaneously, or separately, via the same or different route, at the same or different times. Dosage regimens may be adjusted to provide the optimum desired response (e.g., release rate, a therapeutic or prophylactic response).

The composition of the invention may be administered only once, or it may be administered multiple times. For multiple dosages, the composition may be, for example, administered three times a day, twice a day, once a day, once every two days, twice a week, weekly, once every two weeks, or monthly.

The "chitosanase" used in compositions, systems, kits and methods described herein is not particularly limited herein provided it can hydrolyze a chitosan under physiolgical conditions and is pharmacologically acceptable. In accordance with the International Union of Biochemistry and Molecular Biology (IUBMB), chitosanases perform endohydrolysis of beta-1,4-linkages between D-glucosamine residues in a partly acetylated chitosan. See the publicly available online website chem.qmul.ac.uk/iubmb/enzyme/EC3/2/1/132.html. For example, an exemplary chitosanase that is suitable for use as described herein is the mature chitosanase from the *Janthiobacterium* sp. 4239 strain, GeneBank accession number GQ487533 (Johnsen et al., *Microbial Cell Factories* 2010, 9:5).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to the compositions can mean plus or minus a range of up to 20%, preferably up to 10%, more preferably up to 5%.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

As used herein, the terms "treat" and "treatment" refer to therapeutic treatment, as well prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. "Treatment" can also mean prolonging survival as compared to expected survival if not receiving treatment. Those in need of treatment include those already with the disease or condition as well as those prone to having the disease or condition or those in which the disease or condition is to be prevented.

The term "biocompatible" mean that a composition suitable for contact with tissue of a subject, such as a human subject.

All sequence citations, accession numbers, references, patents, patent applications, scientific publications or other documents cited are hereby incorporated by reference.

The following examples are presented in order to more fully illustrate the preferred embodiments of the invention. They should in no way be construed, however, as limiting the broad scope of the invention.

EXAMPLES

Materials and Methods
Biodegradable Hydrogel Preparation

The parameters for formulating the CGP-hydrogel loaded with dexamethasone were selected creating a model formulation for further testing (CGP-Dex-hydrogel). The CGP-Dex-hydrogel was moderately viscous, injectable, and underwent phase transition to a semi-solid gel in about 15 minutes at 37° C. Preparations were made on the day in which they were to be used. Ninety-eight percent deacetylated chitosan (Biosyntech, Québec) was dissolved in 0.2M acetic acid yielding a 3.4% (w/w) chitosan solution. To this solution, water soluble dexamethasone 0.7% (w/w) (D2915, Sigma, St. Louis Mo.) and glycreophosphate (G6501, Sigma, St. Louis Mo.) 9% (w/w) were added. CGP-hydrogel was prepared and maintained at room temperature until it was used.

In Vitro Matrix Degradation and Dexamethasone Release
CGP-Dex-Hydrogel Pellet Preparation:

In order to evaluate CGP-Dex-hydrogel drug release and matrix degradation in the in vitro setting, it was necessary to create uniform samples which could be handled and transferred. To achieve this purpose, solidified CGP-Dex-hydrogel pellets were created. Liquid CGP-hydrogel was allowed to solidify in 1-mL syringes at 37° C. for two hours until solidified. The tips of the syringes were clipped off with a razor and columns of gel were gently extruded. By sectioning these gel columns at 0.1 mL increments, hydrogel pellets were created.

Dexamethasone Release from CGP-Dex-Hydrogel:

An in vitro drug release study was designed to evaluate the release of dexamethasone from the CGP-dex-hydrogel pellets. Individual CGP-Dex-hydrogel pellets were placed into 2-mL microcentrifuge tubes, weighed, and immediately loaded with 1 mL Dulbecco's phosphate buffered saline (PBS). The microcentrifuge tubes were then incubated at 37° C. on a shaker table at 100 rpm. Every 24 hours the pellets were gently removed from the PBS solution and placed into fresh sets of microcentrifuge tubes with 1 mL PBS and incubated as before. The PBS sample solution was collected, 1 mL of 50% ethanol was added and the samples were then stored at 4° C. until analysis by UV spectrophotometry.

Degradation of CGP-Dex-Hydrogel:

To understand the relationship between the release of dexamethasone and the degradation of the CGP-Dex-hydrogel matrix, the conditions of the dexamethasone release experiment were repeated. However, the pellets were collected every 24 hours for 4 days. After collection the pellets were desiccated for 72 hours and weighed. The ratio of solid components remaining was derived by subtracting from the starting pellet weight, the water weight of each pellet which was calculated from the CGP-Dex-hydrogel formula. A ratio was calculated between the initial solid component weight and the ending solid component weight for samples obtained daily over a 4 day period.

In Vivo Dexamethasone Release and Auditory Function Assessment
Experimental Animals:

To assess the CGP-Dex-hydrogel mediated release of dexamethasone in vivo and to assess the safety of this system in an in vivo setting, an animal model was constructed. C57BL/6J mice (Charles River, Wilmington, Mass.) of either sex and weighing 18 to 22 g were used at 6 to 8 weeks of age. Animals care and use was in accordance with the Institutional Animal Care and Use Committee of the University of Pennsylvania. Anesthetic used for all experiments was tribromoethanol. In total, 25 mice were used. The mice were divided into two groups a CGP-Dex-hydrogel placement group (n=20) and a sham surgery group (n=5). Fifteen of the mice in the CGP-Dex-hydrogel placement group were used for quantification of dexamethasone. The remaining 5 mice from this group and the 5 mice from the sham surgery group were used to evaluate the impact of the surgical procedure and of CGP-Dex-hydrogel upon the auditory system.

CGP-Dex-Hydrogel Placement Procedure:

In preparation for detection of dexamethasone in murine perilymph after CGP-Dex-hydrogel placement, a procedure for placement of CGP-Dex-hydrogel was devised. On the left side, a 2 cm post-auricular incision was made and dissection was carried out along the external auditory canal to the bulla. A 1 mm diamond burr was used to create a single burr hole through the bulla just posterior and inferior to the facial nerve. Through this control-hole, the intact stapedial artery and the round window niche and membrane were visualized. Twenty five mice underwent the surgical procedure to this point. For five of the mice (sham surgery group) the incision was then closed and the animals were allowed to recover. For the remaining 20 mice, CGP-Dex-hydrogel was injected directly onto the RWM filling the RWN. The injection was accomplished with the use of a custom-made flame-pulled glass syringe needle using a microcapillary tube flame-puller. The skin incisions were closed with 4-0 silk, and the animals were returned to the animal facility after they fully recovered from the anesthetic agent.

Perilymph and Serum Harvesting Procedures:

Fifteen of the animals which underwent surgical placement of CGP-Dex-Hydrogel were separated into three groups of 5 animals each for sample harvesting on post-operative days 1, 3 and 5. At the time of sample collection, mice were deeply anesthetized. A cardiac puncture was performed to obtain blood for serum drug concentration analysis. The skin overlying the skull was removed and the external auditory canals were transected. Using a pick and fine forceps the tympanic membrane of the left ear was gently removed. The stapes and oval window were exposed after removing the malleus and incus. Perilymph was collected in previously prepared microcapillary tubes which had tips drawn to approximately 20 µm. The tip of the glass microcapillary tube was used to gently displace the footplate of the stapes laterally. The tip of the microcapillary tube was then advanced a few micrometers through the annular ligament and into the scala vestibule. Via capillary action, within a few seconds a target volume of 0.2 to 0.3 µL of perilymph was collected into the capillary tube. Following this, each animal was euthanized by cervical dislocation. Perilymph was transferred to microcentrifuge tubes and weighed to within 0.01 mg. One mg of perilymph corresponded to 1 µL of perilymph. Samples were stored at −80° C. until they were analyzed.

In order to obtain perilymph samples for analysis, a procedure to collect consistent small sample sizes of perilymph was created. Special attention to collection methods is necessary to insure the quality of data generated. This is because in mice one must consider the potential which exists for contamination of perilymph samples with cerebrospinal fluid. This contamination can potentially occur because of an existing anatomical communication with the CSF space, the cochlear aqueduct. In mice and lower mammals, the cochlear aqueduct remains patent, this is not normally the case for humans. To prevent skewed data as a result of contamination we devised a way to rapidly harvest perilymph in consistent volumes which was well below the average volume of the perilymphatic space in our murine model.

Dexamethasone Concentration in Perilymph and Serum:

To elucidate whether dexamethasone was released into murine perilymph after surgical placement of CGP-Dex-hydrogel and the time-based release kinetics, we analyzed the harvested perilymph samples by liquid chromatography (LC) and mass spectroscopy (MS). Also, to prove that the concentration of dexamethasone was elevated in the local environment compared to systemic distribution, serum samples were also analyzed by LC/MS for comparison. Harvested perilymph and serum samples were analyzed using a Finnigan LTQ linear ion trap mass spectrometer (Thermo Fisher Waltham, Mass.) equipped with an electrospray ionization source. LC separations were conducted with a Zorbax 300Extend-C18 column (125 Å, 3.5µ, 150×2.1 mm i.d., Agilent Santa Clara, Calif.) using a linear gradient of 5 mM ammonium acetate in water-methanol with a flow rate of 250 µL/min Perilymph and serum samples were added with flumethasone (F9507 Sigma St. Louis, Mo.) as an internal standard. The sample cleanup was performed with liquid-liquid extraction using ethyl acetate. LC-MS/MS analyses were conducted using positive electrospray ionization in the monitoring MRM mode using following ion transitions: m/z 393.2→373.1 (dexamethasone), m/z 411.2→391.1 (flumethasone).

Auditory Function Assessment:

To address the safety of CGP-Dex-hydrogel and the procedure to apply the hydrogel an assessment of auditory function using the auditory brainstem response (ABR) was performed to compare thresholds at three timepoints: pre-operative, immediate post-operative (post-op day 2) and late post-operative periods (post-op day 10). ABRs were recorded using a Tucker Davis System II (Tucker-Davis Technologies, Alachua, Fla.). Ten mice were divided into two groups, a CGP-Dex-hydrogel group (n=5) and sham surgery group (n=5). One animal was lost from the sham surgery group before testing on the final day of the experiment. Mice were anesthetized and electrodes were placed at the vertex (active), in the neighborhood of the left postauricular bulla (reference), and in the flank (ground). The acoustic stimulus, generated by the TDT SigGen system consisted of 10 msec tone pips at 16.0 kHz, 24.0 kHz, 32.0 kHz, and 40.0 kHz presented at a rate of 20/sec Responses were averaged over 500 stimuli and intensity increments were set at 5 dB. Threshold was determined to be halfway between the intensity at which an observable response could be detected and the next lower intensity at which no response was visible. Absolute stimulus intensities were calibrated to obtain the sound pressure level in dB relative to 20 µPa.

Statistical Analysis

Statistical analysis was performed with Statmost (Dataxiom Software, Los Angeles, Calif.). The data presented represent the mean of each group +/− standard error of the mean. The statistical test of significance was the Mann-Whitney U test. A conservative probability (P) value less than 0.01 was considered to be statistically significant.

Example 1

In Vitro Matrix Degradation and Dexamethasone Release

Degradation of CGP-Dex-Hydrogel: In vitro experiments demonstrated that 92% of the solid hydrogel matrix remained at 24 hours and then slowly degraded to 16% of the original solid component by day 4. These experiments were duplicated and the average results were plotted (FIG. 1). Results were consistent between experiments with 2.6%<SEM>0.02%.

Figure 2:
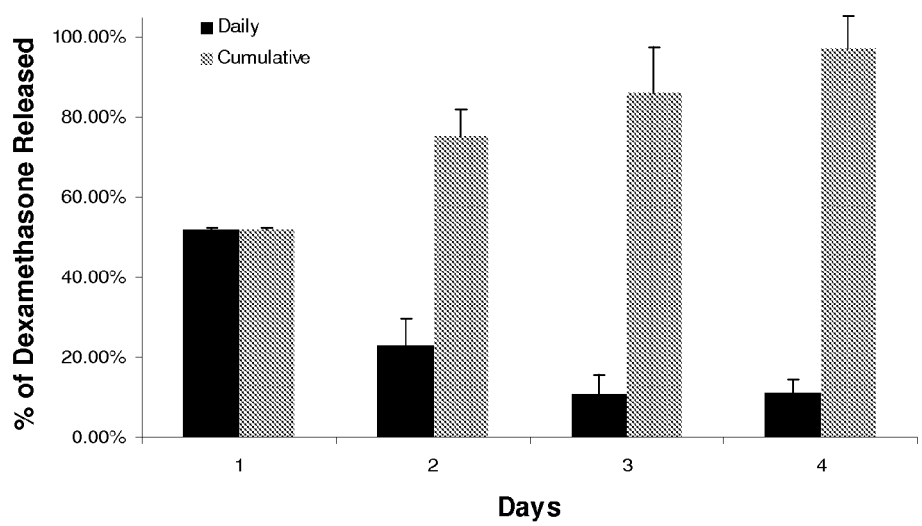
FIG. 2 shows CGP-Dex-Hydrogel release of dexamethasone in a Controlled Manner. Release of dexamethasone occurs for 4 days. The black bars represent the daily measurement and the gray bars the accumulation over the 4 days of testing. There is an initial bolus release of dexamethasone in the first 24 hours followed by a tapering off over the next three days so that by day 4 ~100% of the available dexamethasone has been released. The error bars represent the SEM (±0.004 to 0.114).

Dexamethasone release from CGP-Dex-hydrogel: Sustained release of dexamethasone was observed over 4 days in vitro. In the first 24-hour period there was an initial bolus release of dexamethasone followed by a tapering of drug release until 100% of the drug was released by day 4. The experiment was repeated and the average results were plotted (FIG. 2). The initial bolus release of dexamethasone is likely due to the release of dexamethasone from the voids formed in the hydrogel matrix while the gel was solidifying. The dexamethasone released over the next 3 days represents drug that was interacting more tightly with the matrix through non-covalent molecular interactions. Results were consistent between experiments with 11.4%<SEM>+/−0.04%

Example 2

In Vivo Dexamethasone Release and Auditory Function Assessment

CGP-Dex-Hydrogel Placement Procedure: Twenty five animals successfully underwent the procedure; 20 received CGP-Dex-hydrogel and 5 received no hydrogel injection (sham surgery). There were no surgical complications, the animals recovered normally and there were no infections. Following recovery and for the duration of the experiments, no animals exhibited signs of distress nor were there were no observable pathologic changes in behavior, such as log rolling or circling, indicating that both vestibular and auditory functions were preserved.

Perilymph and Serum Harvesting Procedures: The mean volume of perilymph harvested was $0.22 \ \mu L \pm 0.07 \ \mu L$. There were no statistical differences between groups or between the averages of all samples ($p>0.05$). Day 1: $0.25 \ \mu L \pm 0.07 \ \mu L$; Day 3: $0.20 \ \mu L \pm 0.06 \ \mu L$; Day 5: $0.22 \ \mu L \pm 0.07 \ \mu L$. The volume of serum harvested for each animal was $5 \ \mu L$.

Figure 3:
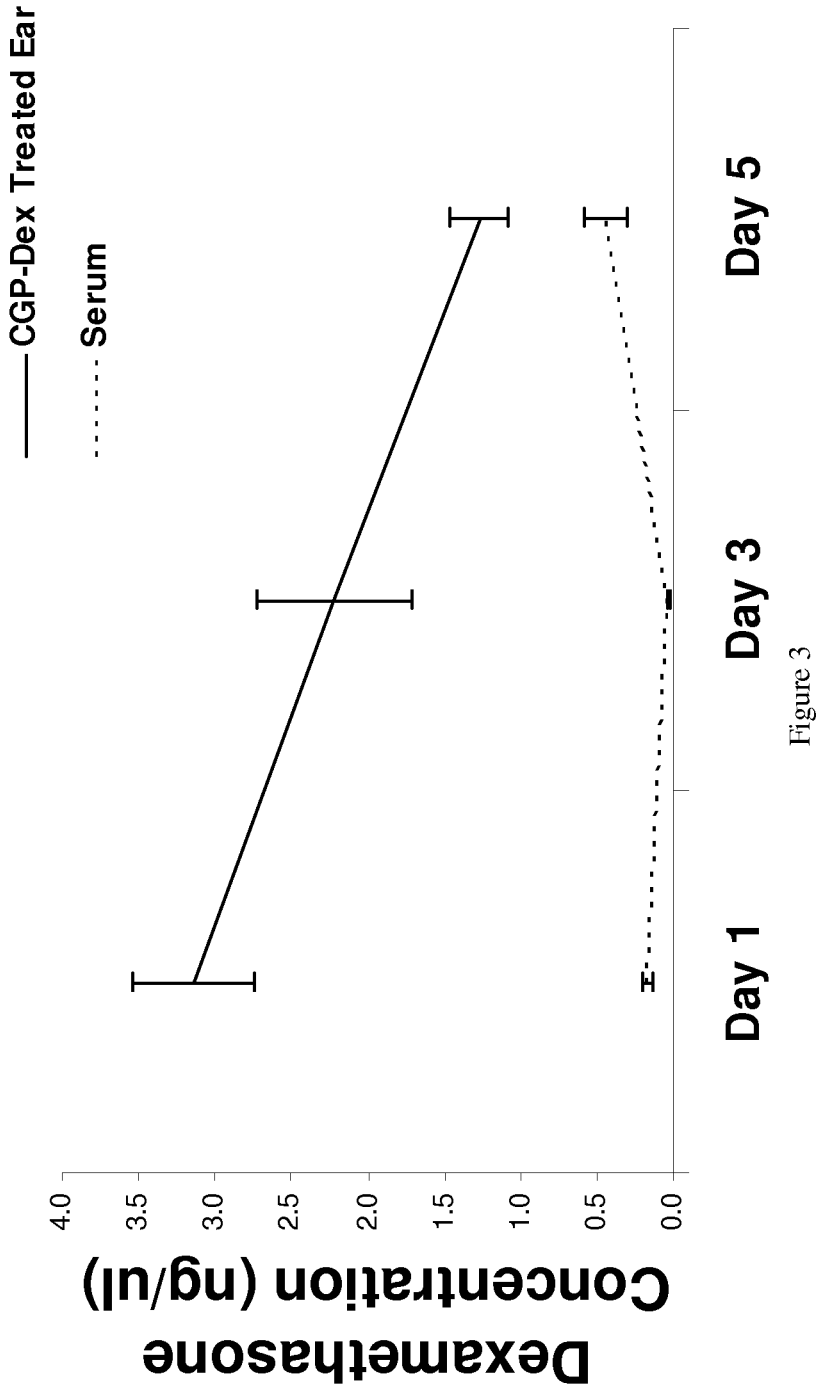
FIG. 3 shows CGP-Dex-Hydrogel locally delivery of Dexamethasone into Perilymph. The release of dexamethasone into perilymph was detected for 5 days. There was a significant difference between dexamethasone levels detected in the treated ear and serum for all time points. (Day 1 and 3 $p<0.01$ Day 5 $p<0.05$) The error bars represent the SEM (+/−0.002 to 0.509).

Dexamethasone Concentration in Perilymph and Serum: Dexamethasone was detected in the perilymph of treated ears. The average dexamethasone concentration within the perilymph peaked at 24 hours at $3.2 \ ng/\mu L$ and declined in a linear fashion over the 5 days of the experiment to $1.3 \ ng/\mu L$. These values remained elevated compared to serum (FIG. 3). There was statistical significance between detected dexamethasone levels of the treated ear and serum of animals for all time points (Day 1 and 3 $p<0.01$ Day 5 $p<0.05$).

Figure 4:
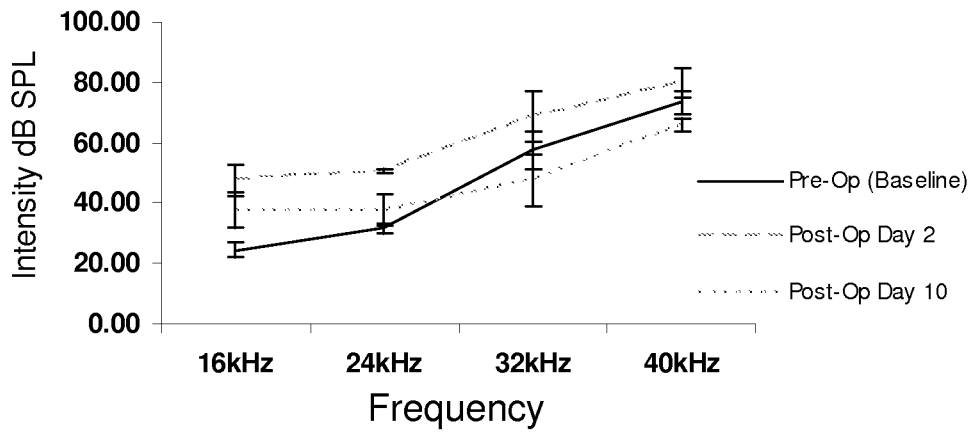
FIG. 4 shows normal hearing following CGP-Dex-Hydrogel Placement. (Top Panel) The solid line represents the pre-operative baseline ABR value of the sham surgery group. There was a 5 to 20 dB increase in hearing thresholds across frequencies in the immediate post-operative period (dashed line). By post-operative day 10, the hearing thresholds returned to baseline levels (dotted line). At the conclusion of the experiment, there was no statistical difference between pre-operative ABR values and those obtained 10 days after the sham surgery. ($p<0.05$) (Bottom Panel) The same pattern was observed in the CGP-Dex-hydrogel group. There was a 5 to 20 dB increase in hearing thresholds across frequencies in the immediate post-operative period (dashed line). By post-operative day 10, the hearing thresholds returned to baseline levels (dotted line). At the conclusion of the experiment, there was no statistical difference between pre-operative ABR values and those obtained 10 days after placement of CGP-Dex-hydrogel. ($p<0.05$). Frequencies tested are within the normal hearing range of mice. The error bars represent the SEM.
Figure 4:
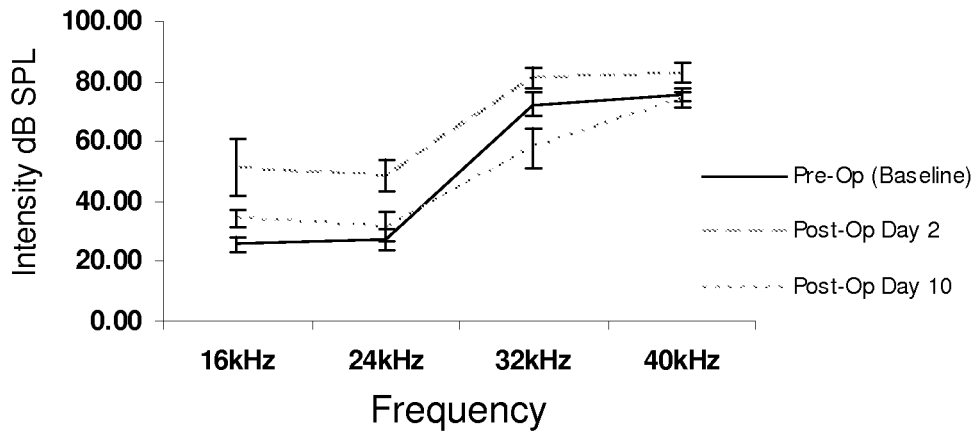

Auditory Function Assessment: There was an initial increase in ABR thresholds followed by recovery of auditory function in both the sham surgery and the CGP-Dex-hydrogel placement groups. (FIGS. 4a and 4b). The pure-tone average at pre-treatment testing across all 4 frequencies tested for the sham surgery group (n=5) and CGP-Dex-hydrogel groups (n=5) respectively were 46.7 and 50.2 dB SPL. Measurement at post-operative day 2 showed a 15.1 and 15.8 dB SPL elevation in hearing threshold for the sham surgery and CGP-Dex-hydrogel groups. By post-operative day 10, the hearing thresholds returned to baseline levels 47.2 for the sham surgery group (n=4) and 49.5 for the CGP-Dex-hydrogel group (n=5). There was no statistical difference between post-operative day 10 measurements and the pre-treatment baseline levels $p>0.05$. There was no statistically significant difference between hearing thresholds of the sham surgery and CGP-Dex-hydrogel groups at any tested frequency with the exception of the measurement at 40 kHz where there was a slight difference ($p<0.05$). One animal from the sham surgery group was lost due to anesthetic overdose at the time of testing on post-operative day 10.

Example 3

A Regulated Delivery System for Inner Ear Drug Application

As shown in the previous examples above an inner ear drug delivery system using a chitosan glycerophosphate (CGP) hydrogel loaded with commonly used drugs for inner ear diseases and it significantly improved the drugs' sustained delivery. The goal of this study is to investigate if the sustained CGP inner ear drug delivery system can be regulated when side effects and potential ototoxicities appear during treatment. The novel delivery system was tested with the gentamicin inner ear application following CGP delivery with/without regulation. This study shows that that the chitosanase-based regulation system can be effectively used for controlled inner ear drug delivery. This system can stop inner ear drug application when side effects or drug-related ototoxicities start to occur and could be used for safe drug delivery for the inner ear application. Specifically, this system could act as an "off" switch for the CGP-hydrogel delivery system in vivo to control, for example, the gentamicin perilymph concentration and distribution.

Materials and Methods Plasmids and Protein Extraction

Figure 6:
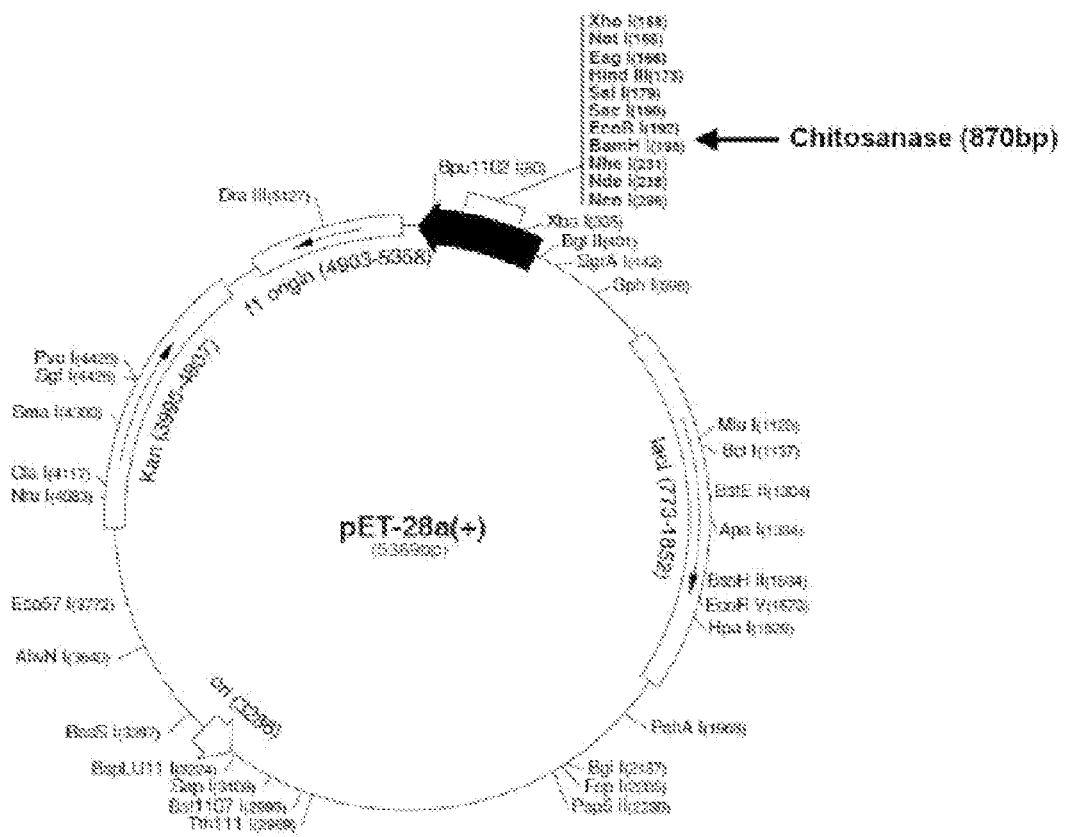
FIG. 6. pET-28a-Chitosanase. The chitosanase coding sequence (870 bp) was cloned between BamH I and EcoR I sites and was confirmed by sequencing.

We obtained the plasmid pBMS172 as a gift from Peter Stougaard (Denmark) (Johnsen et al., *Microbial Cell Factories* 2010, 9:5). In this plasmid the chitosanase gene from pET-28a-Chitosanase was fused with *E. coli* ompA sequence, substituting the native *Janthiobacterium* sp. 4239 signal sequence. In order to purify chitosanase protein, a His-tag was added N terminus (FIG. 6). Standard methods were used to induce the synthesis of protein, followed by its extraction from the bacterial pellets, and purification using the Bug Buster protein extraction reagent (EMD Millipore), and a His-bind Purification Kit (Novagen, EMD Millipore), respectively, according to the manufacturer's instructions.

SDS-PAGE Analysis and Western Blot

To confirm the target protein was being synthesized we performed a SDS-PAGE gel analysis of the crude protein extract. Briefly, samples were run on a SDS-PAGE gel, followed by staining with Coomassie Brilliant Blue R-250 (Sigma). Purified product was confirmed to contain the interested chitosanase-His-tag protein by western blot. Polyclonal rabbit anti-His antibody (Cell Signaling, #2365) was used as primary antibody (1:2000 dilution) to confirm the presence of purified chitosanase. A goat anti-rabbit IgG-HRP (H&L) antibody (Cell Signaling, #7074) was used as secondary antibody (1:10,000 dilution). MagicMark XP western protein standard (Invitrogen, #LC5602) was used as a molecular weight marker. Gels and films were scanned using a Microtek scanner (Microtek).

Concentration and In Vitro Activity of the Purified Chitosanase.

The BCA Protein assay (Thermo Scientific) was used to test the concentration of the purified chitosanase. According to the previous reports, the chitosanase activity is measured in terms of the amount of reducing sugars released during the hydrolysis of colloidal chitosan. The reaction mixture, containing 1 mL of McIlvaine's buffer, 0.5 mL of 3.8% (wt/wt) colloidal chitosan and 0.5 mL chitosanase, was incubated at 46° C. for 30 min. The mixture was then boiled for 10 min to stop the reaction. The amount of reducing sugars released in the supernatant was measured by a method that uses 63% dinitrosalicylic acid (DNS), and the absorbance was measured at 540 nm. A standard curve for glucosamine (GlcN) was created in parallel to measure the amount of GlcN released. One unit (U) of chitosanase activity was defined as the amount of enzyme which catalyzed the release of 1 µmol of reducing sugars in 1 min. The pH of the final product of the reaction was measured using the FISHER Alkacid® Full Range pH kit (Thermo Fisher Scientific).

In Vitro Regulation of Gentamicin Release from the CGP-Hydrogel Thermosensitive Hydrogel Preparation A 2% CGP-hydrogel was prepared essentially as described with the following modifications. Briefly, chitosan (91.2% DDA, Ultrasan, Biosynthec) was dissolved in 0.1M HCl to obtain a 2% w/v chitosan solution by slowly adding the chitosan and stiffing for 20 min until a clear moderately viscous gel was formed. Next, an aqueous solution of 100 mg/mL of Gentamicin sulfate (Sigma, G1264) was slowly loaded to the chitosan solution and stirred for 10 minutes. A 55% w/v water soluble glycerol-2-phosphate (GP) (Sigma, G6251) was prepared separately. Both solutions were kept on ice or at 4° C. until use. To achieve the chitosan crosslinking and "trap" the gentamicin, the GP solution was slowly added dropwise with stirring until a pH of 7.10-7.20 was reached. The CGP-Gentamicin hydrogel (CGP-GENT) solution was kept on ice or at 4° C. until it was used.

In Vitro Model

We designed an in vitro model that closely resembled the middle ear to inner ear drug delivery, consisting of a 1 mL U-100 Insulin Syringe with Slip Tip (BD, Beckton, Dickinson and Company) custom cut with a razor to the level of 0.3 mL. The syringe's tip was sealed with parafilm and a volume of 0.1 mL of the CGP-GENT hydrogel was carefully and quickly loaded with a 3 mL syringe and a 20 µL pipette tip. Each model was incubated at 37° C. for 30 min to allow solidification to occur. The parafilm was then removed carefully not to disrupt the surface of the gel. The syringe was placed tip-down in a 1.5 mL Eppendorf Centrifuge tube containing 200 uL of 1× Dulbecco's Phosphate Buffer Solution (PBS), making sure only the gel surface on the tip side of the model was in contact with the PBS. A total of 6 syringe models divided into 2 groups were used. One group (n=3) was treated by micropipetting 0.1 mL of chitosanase onto the gel. The other group (n=3) was "mock" treated with 1×PBS. The tubes were placed in a C24 Incubator Shaker (New Brunswick Scientific) at 100 rpm at 37° C. until the collection and replacement of the PBS at the desired time points. Samples of the PBS solution were collected at days 0 (before adding the enzyme), 2, 3, 4 and 5.

Quantification of Gentamicin Concentration

The gentamicin concentration was determined by liquid chromatographic-tandem mass spectrometry (LC-MS/MS) as described in our previous study. Briefly, an Accela LC system (Thermo Fisher Scientific)) and TSQ Quantum Ultra equipped with an electrospray ionization source (Thermo Fisher Scientific) was used. Gentamicin separation was achieved on an Ace 5 C 18 column (2.1×75 mm ID.; particle size, 5um) with its guard column (2.1×12.5 mm; MAC-MOD Analytical). Mobile phase A comprised 0.1% heptafluorobutyric acid in water, whereas that of B was 0.1% heptafluorobutyric acid in acetonitrile. Mobile phase gradient program was used: 0 minute, 90:10 (A/B); 3 minutes, 20:80 (A/B); 4 minutes, 20:80 (A/B); 4.01 minutes, 90:10 (A/B); 5 minutes, 90:10 (A/B), with a flow rate of 200 µL/min. The LC-MS/MS analyses were conducted in selected-reaction monitoring mode with the following ion transition: m/z 464>322 used for analyte identification and quantification, whereas 3 ion transitions m/z 464>160 were used for confirmation of the presence of gentamicin in the test sample.

In Vivo Assessment of the Regulatory Effect of Chitosanase on the CGP-GENT Delivery System Preparation of the Biodegradable Hydrogels For the pharmacokinetic experiments, the CGP-GENT was prepared on the day in which it was to be used as previously described. The final solution contained approximately 3.8% (w/v) chitosan, 18.1% (wt/wt) GP, and the concentration of gentamicin was approximately 200 mg/mL.

For the distribution experiments a purified Texas Red-labeled gentamicin (GTTR) conjugate was obtained as a kind gift from Peter Steyger (Portland, Oreg.) Immediately before surgery, 5 µL of CGP was carefully mixed with 21.25 µg of GTTR by stiffing for approximately 1 minute, followed by centrifugation at 14,000 rpm for 30 seconds to obtain a final concentration of 4.25 µg/µL CGP-GTTR hydrogel.

Mouse Model

A total of 50 C57BL/6J mice (Charles River, Wilmington, Mass., USA), 6 to 8 weeks of age, of either gender, weighing 18 to 22 g were used Animal care and use was in accordance with the Institutional Animal Care and Use Committee of the University of Pennsylvania. Anesthesia was achieved by intraperitoneal injection of 0.4-0.6 mg of Avertin (T48402; Sigma) in all experiments. The mice were randomly divided into 4 groups: a CGP-GENT group (n=20), a CGP-GENT+chitosanase group (n=20), a CGP-GTTR group (n=5), and a CGP-GTTR+chitosanase group (n=5).

Hydrogel and Chitosanase Application

After anesthesia, a retroauricular incision was made to approach the temporal bone in the left ear. Using a microsurgical approach, a hole was drilled through the bulla with a 1-mm diamond burr to expose the RWN. In both groups, 0.2 µl of CGP-GENT (200 mg/µL) was carefully applied to the RWN using a custom-made flame pulled glass syringe needle, for a total dose of 40 ug of gentamicin. In the CGP-GENT+chitosanase group, mice were applied approximately 1 µL chitosanase (1.8 mg/mL) to the posterior part of the middle ear just covering the RWN 24 hours after the injection of the CGP-GENT-hydrogel.

Figure 7:
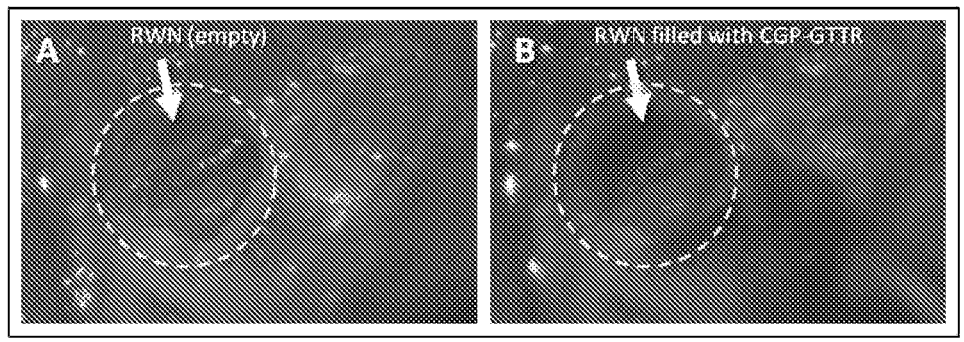
FIG. 7. CGP-GTTR application. A) Exposure of the middle ear (dashed circle) showing the RWN (arrow) before placement of the CGP-GTTR. B) Application of the CGP-GTTR hydrogel onto the RWN (arrow) using a custom-made flame pulled glass syringe.

For the gentamicin distribution experiments we followed the same procedures as above with the following modifications. On the first day, surgery was performed in both ears and approximately 0.3 uL was carefully place on the RWN (FIG. 7) and allowed to solidify for 24 hours. At this time, the left RWN was re-exposed and approximately 1 µL of chitosanase was applied.

Perilymph and Plasma Harvesting

For the kinetic analysis, perilymph and blood samples were harvested from 5 mice from each group at 4 time points: postoperative days 1, 3, 5, and 7. The procedures were performed under anesthesia, as described in our previous study, with the following modifications. The blood was obtained through a jugular vein puncture with an incision on the neck before the collection of the perilymph. While under deep anesthesia the mice were euthanized and the cochleae were quickly dissected off from the temporal bone to allow for the collection of approximately 0.3 µL of perilymph from the oval window (OW) with custom-made microcapillary tubes marked with a scale at 0.3 µl. All the samples were stored at −80° C. until they were analyzed.

Tissue Harvesting and Preparation

At the designated time points the mice were euthanized and the temporal bones on both sides were immediately dissected, the stapes removed from the OW and both the cochlea and vestibular systems were locally perfused and immersion fixed in 4% paraformaldehyde/PBS. The tissues were kept in the fixative at 4° C. in the dark until processing. Samples were processed by the surface preparation technique.

Fluorescence Microscopy

Following careful dissection, the membranous cochlea and vestibular organs were decalcified in 0.5M EDTA, pH 8 for one hour at room temperature. The tissues were then washed in PBS and incubated with Phalloidin-FITC (Sigma, P5282) to label the hair cells of the inner ear at a concentration of 1 ug/mL in PBS for 30 min at room temperature. The tissues were mounted on slides using Vectashield containing DAPI (VectaLab, H-1200). Fluorescence microscopy images were captured using a Nikon Eclipse Ti Inverted Microscope System (Nikon) and NIS-Elements (Nikon).

Statistics

Statistical analysis was performed with SAS version 9.2 mixed procedure. The statistical tests of significance were multi-factor analysis of variance. P-value less than 0.05 was considered statistical significant.

Results

Successful Purification of Chitosanase

Figure 8A:
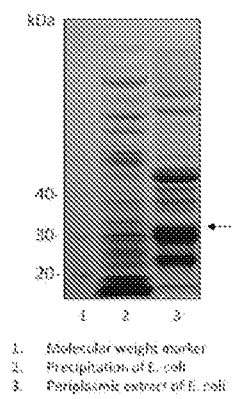
FIG. 8. Protein extraction and purification. A) SDS-PAGE gel analysis of crude protein showing a band at around 33 kDa (arrow), which corresponds to the molecular weight of chitosanase. B) Western blot analysis after purification. An anti-His-tag antibody was used and the result showed a band near the corresponding molecular weight of chitosanase (arrow), confirming its purification.
Figure 8B:
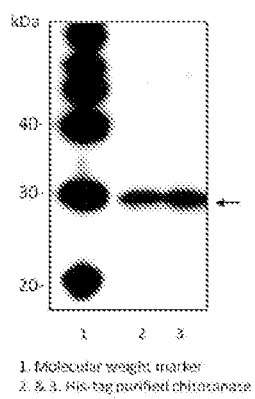

The insertion of the chitosanase gene was confirmed by sequencing. Transformants showed haloes around the colonies, suggesting that the fragment encoded a polypeptide with chitosanase activity. The SDS-PAGE gel analysis revealed that the mature secreted product, found in the periplasm of BMS172 isolated from the E. coli growth medium, migrated to a position corresponding to that of the native chitosanase product of 33 kDa (FIG. 8A). Purification was confirmed using western blot analysis (FIG. 8B). The purified chitosansase was aliquoted into several 15 mL tubes with concentrations ranging from 1.26-1.8 mg/mL.

Activity of the Chitosanase In Vitro

The chitosanase dissolved the 3.8% chitosan easily. It digested most of the same volume of 3.8% chitosan in 30 min at 37° C. compared to the controls treated only with purified deionized water, which remained in a semi-solid state. The pH value of the dissolved solutions ranged between 6.5 and 7.

The Addition of Chitosanase "Empties" the CGP-GENT Hydrogel In Vitro

Figure 9:
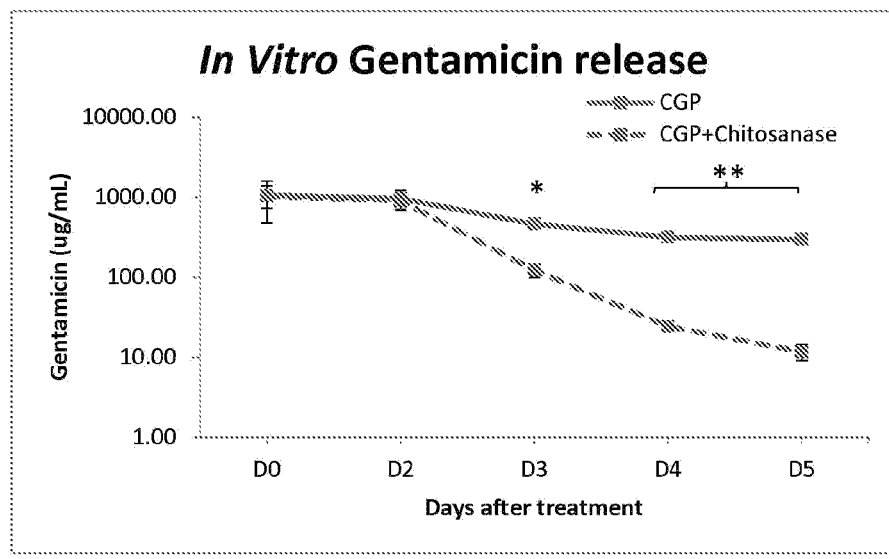
FIG. 9. Chitosanase effectively stops the gentamicin release in vitro. The addition of chitosanase to the CGP-GENT hydrogel results in a rapid release of the gentamicin from the system. By D3 the concentration was significantly reduced by 73.6% (*$P<0.05$). By D4 and D5 the concentrations reduced by more than 90% (**$P<0.001$). Mean concentrations of gentamicin of at least 3 samples are shown. The error bars represent the standard error of the mean (SEM).

As shown in FIG. 9, after day 2 (D2), the concentration of gentamicin in the chitosanase group dropped to significantly lower levels, compared to the continued steady concentration in the control group. Beginning at day 3 (D3), the concentrations were reduced by 73.6% (P<0.05). On days 4 and 5 (D4 and D5) they were reduced by 92.3% and 96.1%, respectively.

The Chitosanase Effectively Stops the CGP-GENT Delivery System In Vivo

Figure 10:
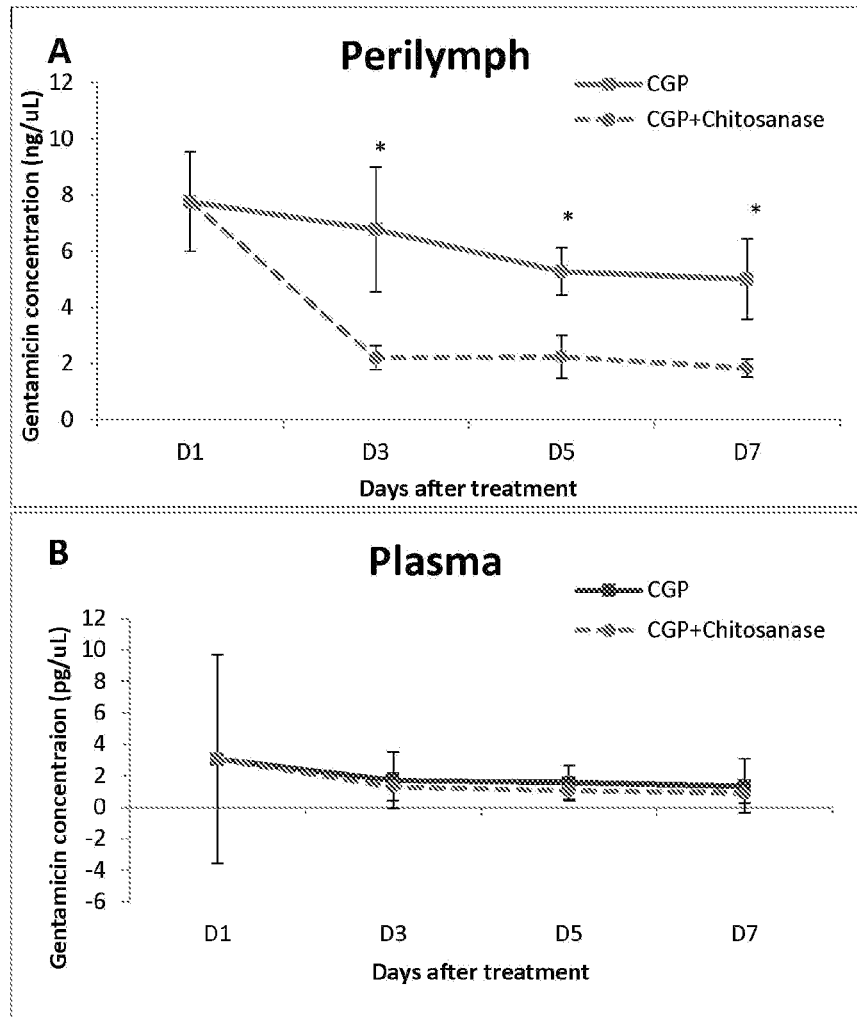
FIG. 10. Comparison of the concentration curves of gentamicin in CGP-GENT and CGP-GENT+chitosanase treated ears. A) The perilymph concentration of gentamicin was determined to be in the ng/μL range and it showed a significant difference in the gentamicin concentration (P<0.05) between the two groups after D3. B) In the blood samples, however, the concentration was in the pg/μL range and there was no significant difference between the groups. Mean concentrations of at least 3 samples are shown. The error bars represent the standard error of the mean (SEM).

There were no surgical complications or infections noted in any of the animals. Following recovery and for the duration of the experiments, no animals exhibited signs of distress and there were no observable signs of vestibulopathy, such as log rolling or circling. The results of the experiment are summarized in FIG. 10. The concentration of gentamicin in the perilymph of the control group decreased smoothly from the beginning, whereas in the chitosanase group ears, the concentration decreased sharply starting at D3 (48 hours after applying the chitosanase). There was significant difference between the two groups after D3 (P<0.05). The plasma concentration was very low in both groups and there was no significant difference between them (P>0.05).

Distribution of GTTR Following CGP Delivery

Figure 11:
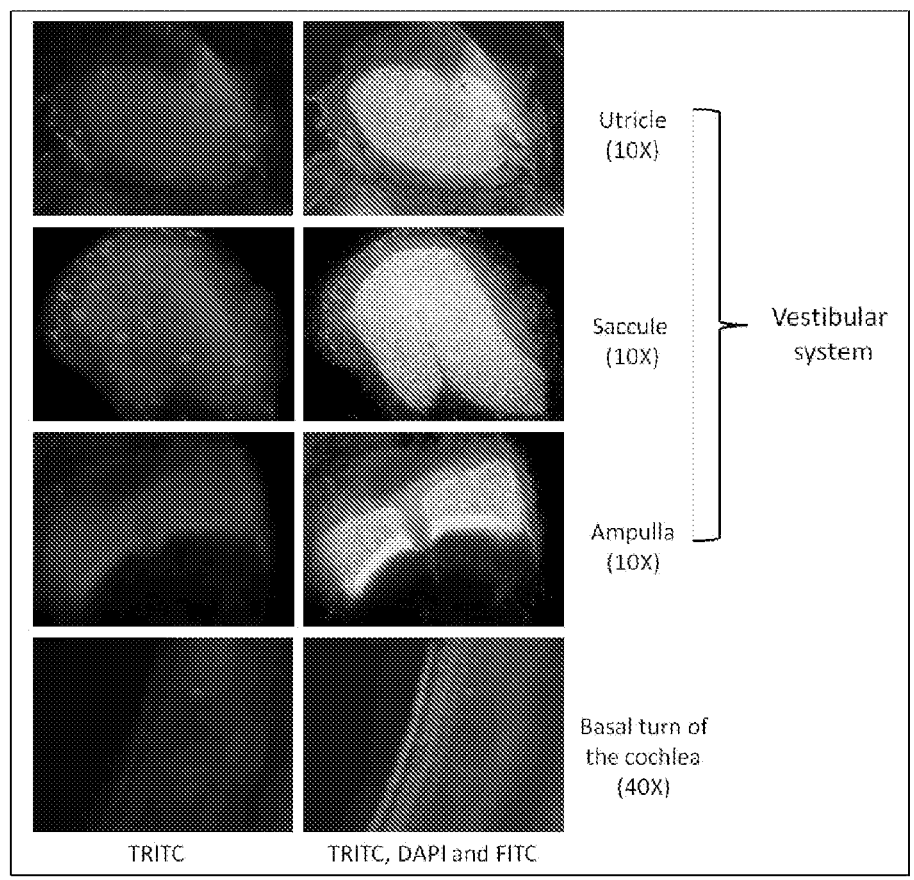
FIG. 11. Vestibular-dominant distribution of GTTR. Histologic studies revealed a predominant GTTR distribution in the vestibular system using CGP-GTTR delivery evaluated by the TRITC (red) signal in the vestibular system (utricle, saccule, ampulla) as compared to the basal turn of the cochlea. The results were consistent in samples collected at different time points. Representative images taken 48 hours after CGP-GTTR application are shown.
Figure 12:
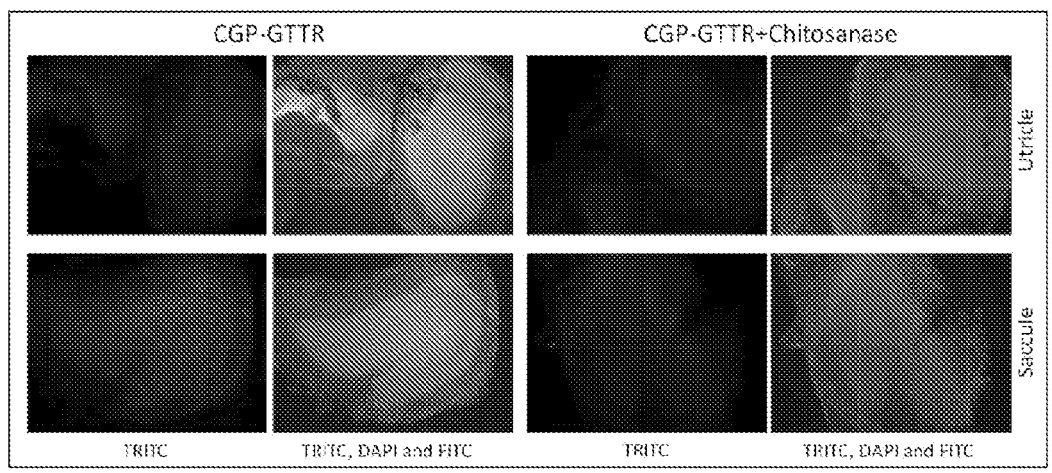
FIG. 12. Chitosanase affects the GTTR intensity following CGP-GTTR delivery. Images of both groups were taken under the same conditions. Both vestibular organs show a diminished TRITC (red) signal in the CGP-GTTR+Chitosanase group at day 4 after chitosanase application.

As illustrated in FIG. 11, the CGP-GTTR delivery results in a vestibular dominant distribution, demonstrated by the TRITC signal intensity. We evaluated the utricles, saccules and ampullae organs (vestibular system), and the basal turn of the cochlea at days 1, 2, 3, 7 and 9. All time points followed a similar pattern. The chitosanase significantly diminished the TRITC signal intensity beginning at day 4 as shown in FIG. 12.

In summary, we have developed an effective, safe method to enzymatically regulate a chitosan-based inner ear drug delivery system by using chitosanase. We successfully obtained a purified enzyme and tested its concentration and function. Finally, we were able to effectively stop the delivery of gentamicin to the inner ear by introducing this enzyme to our system.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A system for controlled release delivery comprising:
   (i) a chitosan glycerophosphate (CGP) hydrogel comprising at least one agent effective in the treatment of otorhinolaryngology-associated pathology, or Head and Neck associated pathology; and
   (ii) a chitosanase present in an amount effective to dissolve the CGP hydrogel and thereby release the agent associated with the CGP hydrogel.

2. The system of claim 1, wherein said hydrogel and said chitosanase are each formulated for administration to an inner ear of a subject.

3. The system of claim 1, wherein said hydrogel and said chitosanase are each formulated for administration to a round window membrane of a subject.

4. The system of claim 1, wherein said CGP hydrogel comprises 2-10% (w/w) chitosan.

5. The system of claim 1, wherein said CGP hydrogel comprises 5-30% (w/w) glycerophosphate.

6. The system of claim 1, wherein said hydrogel releases said agent over a period of no less than 24 hours.

7. The system of claim 1, wherein the amount of said chitosanase is sufficient to release at least 90% of said agent within a period of no more that 24 hours.

8. The system of claim 1, wherein the CGP hydrogel is comprised of a first CGP hydrogel having a first chitosan to glycerophosphate ratio; and a second CGP hydrogel having a second chitosan to glycerophosphate ratio, wherein the first chitosan to glycerophosphate ratio is different from the second chitosan to glycerophosphate ratio.

9. The system of claim 1, wherein said at least one agent is a steroid, an antibiotic, or a combination thereof.

10. The system of claim 9, wherein said at least one agent is gentamicin.

11. The system of claim 9, wherein said at least one agent is streptomycin.

12. The system of claim 9, wherein said drug is dexamethasone.

13. The system of claim 1, wherein said at least one agent is a drug for an inner ear disease.

14. The system of claim 13, wherein said at least one agent is a drug for Ménière's disease.

15. A method for treating an inner ear disease, comprising the steps of:
   (i) administering to a subject in need thereof a chitosan glycerophosphate (CGP) hydrogel comprising at least one agent effective in the treatment of an inner ear disease, and
   (ii) administering a chitosanase to the inner ear of the subject, wherein the administration of said chitosanase dissolves the CGP hydrogel and releases the agent associated with said CGP hydrogel.

16. The method of claim 15, whereby said subject is human.

17. The method of claim 15, whereby said administering steps comprise applying said CGP hydrogel and said chitosanase to a round window membrane of the subject.

18. The method of claim 15, whereby said inner ear disease is Ménière's disease.

19. The method of claim 15, whereby step (ii) is performed following an ototoxicity induced by said agent.

20. The method of claim 15, whereby step (ii) is performed following a disappearance of at least one symptom of said disease.

21. A method for regulating the treatment of an inner ear disease, comprising the steps of:
  (i) administering to a subject in need thereof a chitosan glycerophosphate (CGP) hydrogel comprising at least one agent effective in the treatment of an inner ear disease, and
  (ii) administering a chitosanase to the inner ear of the subject (e.g., by applying to the round window membrane of the subject), wherein the administration of said chitosanase dissolves the CGP hydrogel and releases the agent associated with said CGP hydrogel.

22. The method of claim 21, whereby said subject is human.

23. The method of claim 21, whereby said administering steps comprise applying said CGP hydrogel and said chitosanase to a round window membrane of the subject.

24. The method of claim 21, whereby said inner ear disease is Ménière's disease.

25. The method of claim 21, whereby step (ii) is performed to stop said treatment.

26. The method of claim 25, whereby step (ii) is performed to stop said treatment to reduce an ototoxicity induced by said agent.

27. The method of claim 25, whereby step (ii) is performed to stop said treatment following a disappearance of at least one symptom of said disease.

28. A method for alleviating a drug induced ototoxicity, the method comprising: administering a chitosanase to an inner ear of a subject having a chitosan-glycerophosphate (CGP) hydrogel based drug delivery system applied to said inner ear, wherein the administration of said chitosanase dissolves said CGP hydrogel and releases said drug associated with said CGP hydrogel, thereby alleviating said drug induced ototoxicity.

29. A method for regulating a drug release from a chitosan-glycerophosphate (CGP) hydrogel in an inner ear of a subject, the method comprising: administering a chitosanase to said inner ear of said subject, wherein the administration of said chitosanase dissolves said CGP hydrogel and removes said drug associated with said CGP hydrogel from said inner ear, thereby regulating said drug release from said CGP hydrogel in said inner ear of said subject.

* * * * *